US009598408B2

(12) United States Patent
Fuchss et al.

(10) Patent No.: US 9,598,408 B2
(45) Date of Patent: Mar. 21, 2017

(54) IMIDAZO[4,5-C]QUINOLINES AS DNA-PK INHIBITORS

(71) Applicant: MERCK PATENT GESELLSCHAFT MIT BESCHRANKTER HAFTUNG, Darmstadt (DE)

(72) Inventors: Thomas Fuchss, Bensheim-Auerbach (DE); Werner Mederski, Zwingenberg (DE); Frank Zenke, Darmstadt (DE)

(73) Assignee: MERCK PATENT GESELLSCHAFT MIT BESCHRANKTER HAFTUNG, Darmstadt (DE)

( * ) Notice: Subject to any disclaimer, the term of this patent is extended or adjusted under 35 U.S.C. 154(b) by 2 days.

(21) Appl. No.: 14/676,125

(22) Filed: Apr. 1, 2015

(65) Prior Publication Data
US 2015/0203491 A1 Jul. 23, 2015

Related U.S. Application Data

(62) Division of application No. 13/819,488, filed as application No. PCT/EP2011/003744 on Jul. 26, 2011, now Pat. No. 9,000,153.

(30) Foreign Application Priority Data

Aug. 28, 2010 (DE) ........................ 10 2010 035 744

(51) Int. Cl.
C07D 417/04 (2006.01)
C07D 215/42 (2006.01)
C07D 215/44 (2006.01)
C07D 215/46 (2006.01)
A61K 31/437 (2006.01)
A61K 31/4745 (2006.01)
A61K 31/5377 (2006.01)
C07D 471/04 (2006.01)
A61K 45/06 (2006.01)

(52) U.S. Cl.
CPC .......... *C07D 471/04* (2013.01); *A61K 31/437* (2013.01); *A61K 31/4745* (2013.01); *A61K 31/5377* (2013.01); *A61K 45/06* (2013.01); *C07D 215/42* (2013.01); *C07D 215/44* (2013.01); *C07D 215/46* (2013.01)

(58) Field of Classification Search
None
See application file for complete search history.

(56) References Cited

U.S. PATENT DOCUMENTS

| 5,444,062 | A | 8/1995 | Coe et al. |
| 7,667,039 | B2 | 2/2010 | Garcia-Echeverria et al. |
| 7,696,203 | B2 | 4/2010 | Smith et al. |
| 7,994,170 | B2 | 8/2011 | Garcia-Echeverria et al. |
| 7,998,972 | B2 | 8/2011 | Garcia-Echeverria et al. |
| 8,431,592 | B2 | 4/2013 | Garcia-Echeverria et al. |
| 8,476,294 | B2 | 7/2013 | Furet et al. |
| 2005/0245562 | A1 | 11/2005 | Garcia-Echeverria et al. |
| 2006/0264427 | A1 | 11/2006 | Smith et al. |
| 2008/0194579 | A1 | 8/2008 | Garcia-Echeverria et al. |
| 2010/0056558 | A1 | 3/2010 | Garcia-Echeverria et al. |
| 2011/0130386 | A1 | 6/2011 | Frigerio et al. |
| 2011/0212053 | A1 | 9/2011 | Qian et al. |
| 2011/0251202 | A1 | 10/2011 | Garcia-Echeverria et al. |
| 2012/0207751 | A1 | 8/2012 | Garcia-Echeverria et al. |

FOREIGN PATENT DOCUMENTS

| CN | 1830964 A | 9/2006 |
| WO | 92/07844 A1 | 5/1992 |
| WO | 03/097641 A2 | 11/2003 |
| WO | 2006/109081 A1 | 10/2006 |
| WO | 2006/122806 A2 | 11/2006 |
| WO | 2009/130469 A1 | 10/2009 |
| WO | 2009/155527 A2 | 12/2009 |

OTHER PUBLICATIONS

International Search Report for PCT/EP2011/003744 (Oct. 7, 2011).
International Preliminary Report on Patentability for PCT/EP2011/003744 (Mar. 5, 2013).
H. Li et al., "Discovering Novel 3-Nitroquinolines as a New Class of Anticancer Agents", Acta Pharmacologica Sinica, vol. 29, No. 12 (Dec. 2008) pp. 1529-1538.
H. Lempiainen et al., "Emerging Common Themes in Regulation of PIKKs and PI3Ks", The EMBO Journal, vol. 28 (2009) pp. 3067-3073.
M. Lavin et al., "The Genetic Defect in Ataxia-Telangiectasia", Annu. Rev. Immunol., vol. 15 (1997) pp. 177-202.
G. Rotman et al., "ATM: From Gene to Function", Human Molecular Genetics, vol. 7, No. 10 (1998) pp. 1555-1563.
K. Rosenzweig et al., "Radiosensitization of Human Tumor Cells by the Phosphatidylinositol 3-Kinase Inhibitors Wortmannin and LY294002 Correlates with Inhibition of DNA-Dependent Protein Kinase and Prolonged G2-M Delay", Clinical Cancer Research, vol. 3 (Jul. 1997) pp. 1149-1156.
I. Hardcastle et al., "Discovery of Potent Chromen-4-One Inhibitors of the DNA-Dependent Protein Kinase (DNA-PK) Using a Small-Molecule Library Approach", J. Med. Chem., vol. 48 (2005) pp. 7829-7846.

(Continued)

*Primary Examiner* — Nyeemah A Grazier
(74) *Attorney, Agent, or Firm* — Millen, White, Zelano and Branigan, P.C.

(57) ABSTRACT

The invention relates to compounds of the formulae (I) and (II) in which R1, R2, R3, R4, R5, R8, X and m have the meaning indicated in the claims, and/or physiologically acceptable salts, tautomers and stereoisomers thereof, including mixtures thereof in all ratios. The compounds of the formula (I) can be used for the inhibition of serine/threonine protein kinases and for the sensitisation of cancer cells to anticancer agents and/or ionising radiation. The invention also relates to the use of the compounds of the formula (I) in the prophylaxis, therapy or progress control of cancer, tumours, metastases or angiogenesis disorders, in combination with radiotherapy and/or an anticancer agent. The invention furthermore relates to a process for the preparation of the compounds of the formula (I).

3 Claims, No Drawings

(56) References Cited

OTHER PUBLICATIONS

M. Yoshida et al., "Study of Biodegradable Copoly(L-lactic acid / glycolic acid) Formulations with Controlled Release of Z-100 for Application in Radiation Therapy", International Journal of Pharmaceutics, vol. 115 (1995) pp. 61-67.
G. Smith et al., "The DNA-Dependent Protein Kinase", Genes & Development, vol. 13 (1999) pp. 916-934.
F. Goytisolo et al., "The Absence of the DNA-Dependent Protein Kinase Catalytic Subunit in Mice Results in Anaphase Bridges and in Increased Telomeric Fusions with Normal Telomere Length and G-Strand Overhang", Molecular and Cellular Biology, vol. 21, No. 11 (Jun. 2001) pp. 3642-3651.
E. Williams et al., "Telomere Dysfunction and DNA-PKcs Deficiency: Characterization and Consequence", Cancer Res., vol. 69, No. 5 (Mar. 1, 2009) pp. 2100-2107.
K. Hartley et al., "DNA-Dependent Protein Kinase Catalytic Subunit: A Relative of Phosphatidylinositol 3-Kinase and the Ataxia Telangiectasia Gene Product", Cell, vol. 82 (Sep. 8, 1995) pp. 849-856.
Izzard et al. "Competitive and Noncompetitive Inhibition of the DNA-dependent Protein Kinase" (Jun. 1, 1999); Cancer Research 59: 2581.
Shanghai Inst of Medicines CHI; "4-Substituting Anilino-3-Nitroquinoline Compounds, Prepn. Method and Use Thereof"; Espacenet; Sep. 13, 2006; English Abstract of CN1830964(A).

IMIDAZO[4,5-C]QUINOLINES AS DNA-PK INHIBITORS

The invention relates to compounds of the formulae (I) and (II)

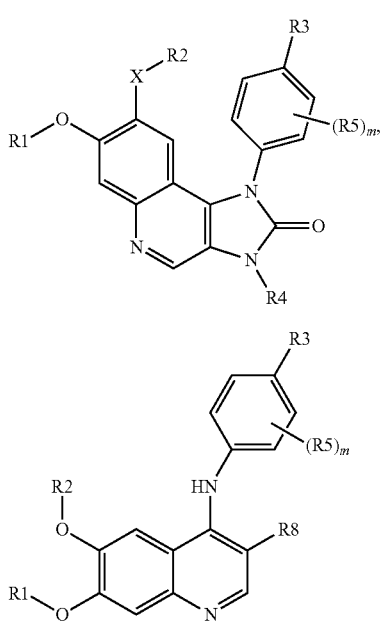

in which R1, R2, R3, R4, R5, R8, X and m have the meaning indicated in the claims, and/or physiologically acceptable salts, tautomers and stereoisomers thereof, including mixtures thereof in all ratios. The compounds of the formula (I) can be used for the inhibition of serine/threonine protein kinases and for the sensitisation of cancer cells to anticancer agents and/or ionising radiation. The invention also relates to the use of the compounds of the formula (I) in the prophylaxis, therapy or progress control of cancer, tumours, metastases or angiogenesis disorders, in combination with radiotherapy and/or an anticancer agent. The invention furthermore relates to a process for the preparation of the compounds of the formula (I) by reaction of compounds of the formula (II) and optionally conversion of a base or acid of the compounds of the formula (I) into one of its salts.

DNA-dependent protein kinase (DNA-PK) is a serine/threonine protein kinase which is activated in conjunction with DNA. Biochemical and genetic data show that DNA-PK consists (a) of a catalytic sub-unit, which is called DNA-PKcs, and (b) two regulatory components (Ku70 and Ku80). In functional terms, DNA-PK is a crucial constituent on the one hand of the repair of DNA double-strand breaks (DSBs) and on the other hand of somatic or V(D)J recombination. In addition, DNA-PK and its components are connected with a multiplicity of further physiological processes, including modulation of the chromatin structure and telomeric maintenance (Smith & Jackson (1999) Genes and Dev 13: 916; Goytisolo et al. (2001) Mol. Cell. Biol. 21: 3642; Williams et al. (2009) Cancer Res. 69: 2100).

Human genetic material in the form of DNA is constantly subjected to attack by reactive oxygen species (ROSs), which are formed principally as by-products of oxidative metabolism. ROSs are capable of causing DNA damage in the form of single-strand breaks. Double-strand breaks can arise if prior single-strand breaks occur in close proximity. In addition, single- and double-strand breaks may be caused if the DNA replication fork encounters damaged base patterns. Furthermore, exogenous influences, such as ionising radiation (for example gamma or heavy-ion radiation), and certain anticancer medicaments (for example bleomycin) are capable of causing DNA double-strand breaks. DSBs may furthermore occur as intermediates of somatic recombination, a process which is important for the formation of a functional immune system of all vertebrates. If DNA double-strand breaks are not repaired or are repaired incorrectly, mutations and/or chromosome aberrations may occur, which may consequently result in cell death. In order to counter the severe dangers resulting from DNA double-strand breaks, eukaryotic cells have developed a number of mechanisms to repair them. Higher eukaryotes use predominantly so-called non-homologous end-joining (NHEJ), in which the DNA-dependent protein kinase adopts the key role. Biochemical investigations have shown that DNA-PK is activated most effectively by the occurrence of DNA-DSBs. Cell lines whose DNA-PK components have mutated and are non-functional prove to be radiation-sensitive (Smith and Jackson, 1999).

Owing to its catalytic domain, which is in the C-terminal catalytic sub-unit (DNA-PKcs), which numbers about 500 amino acids, DNA-PK belongs to the family of phosphatidyl-inositol-3-kinase-related kinases (PIKKs), where DNA-PK is not a lipid kinase (Hartley et al. (1995) Cell 82: 849; Smith & Jackson (1999) Genes and Dev 13: 916; Lempiäinen & Halazonetis (2009) EMBO J. 28: 3067).

The protein kinase ATM (ataxia-telangiectasia-mutated kinase) likewise belongs to the PIKK family. It too has central importance in the recognition of DNA damage. Patients suffering from ataxia telangiectasia exhibit, inter alia, increased sensitivity to ionising radiation. (Lavin & Shiloh (1997) Annu. Rev. Immunol. 15: 177; Rotman & Shiloh (1998) Hum. Mol. Genet. 7: 1555).

It has been described by Izzard et al. (1999) Cancer Res. 59: 2581, that the PI3 kinase inhibitor LY294002 inhibits the function of DNA-PK in in-vitro experiments. The $IC_{50}$ value (concentration at which 50% of the enzyme activity is inhibited) is at a relatively ineffective 1.25 µM (5.0 mM ATP). Although the evidence that the inhibitor LY294002 allows mammal cells to become more radiation-sensitive, i.e. the cytotoxicity of ionising radiation is increased, in principle implies use in the irradiation therapy of, for example, solid cancer tumours, only a weak increase in sensitivity to ionising irradiation has been demonstrated for LY294002 in cellular terms (Rosenzweig et al. (1999) Clin. Cancer Res. 3: 1149). KuDOS Pharmaceuticals Ltd. have optimised the lead structure LY294002 and presented various DNA-PK inhibitors. The introduction of a dibenzothiophenyl group led to the inhibitor NU-7441, an ATP-competitive compound having an $IC_{50}$ value of 20.0 nM (Hardcastle et al. (2005) J. Med. Chem. 48: 7829). KU-0060648 combines inhibitory properties with respect to DNA-PK with an improved solubility profile in aqueous medium, but the kinases of the PI3K isoenzyme family are likewise potently inhibited by KU-0060648. The long-existing need for a potent and selective DNA-PK inhibitor has consequently not been satisfied to date.

The invention is based on the object of overcoming the disadvantages indicated in the prior art and of developing effective inhibitors of DNA-PK which are selective with respect to the related kinases of the PIKK family and are of low molecular size and, in particular, enable effective application in cancer therapy as radio- and chemosensitisers— with the aim of improving the therapeutic efficacy with a simultaneous reduction in side effects.

The object of the invention is achieved in accordance with the independent claims. The sub-claims contain preferred embodiments. In accordance with the invention, compounds of the formula (I) are provided

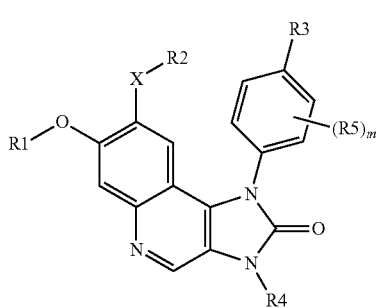

in which
R1 denotes Y or —(CY$_2$)$_n$—Ar,
R2 denotes Y, —(CY$_2$)$_p$—(C[YR6])$_s$—R7 or -alk-R7,
R3 denotes Y or CN,
R4 denotes Y, Hal, —(CY$_2$)$_p$—COOY or —(CY$_2$)$_p$—CO—NYY,
R5 denotes A, Hal, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY,
R6 denotes Y, Hal, —(CY$_2$)$_n$—NYY, —(CY$_2$)$_n$—NY—COO—(CY$_2$)$_n$—SiA$_3$, —(CY$_2$)$_n$—COOY, —CO—NYY, —CO—NY—(CY$_2$)$_n$—OY, —CO—NY—(CY$_2$)$_n$—NYY or SO$_2$A,
R7 denotes —(CY$_2$)$_p$—Ar or —(CY$_2$)$_p$-Het$^1$,
X denotes CH$_2$, O, S or a single bond,
Y denotes H or A,
A denotes unbranched or branched alkyl having 1, 2, 3, 4, 5, 6, 7, 8, 9 or 10 C atoms, where 1, 2, 3, 4, 5, 6 or 7H atoms may be replaced, independently of one another, by Hal,
Alk denotes alkenyl having 1, 2, 3, 4, 5 or 6 C atoms, where 1, 2, 3 or 4 H atoms may be replaced, independently of one another, by Hal and/or OY,
Ar denotes phenyl which is unsubstituted or mono-, di- or trisubstituted by Hal, A, CN, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY,
Het$^1$ denotes mono- or bicyclic heteroaryl having 2, 3, 4, 5, 6, 7, 8 or 9 C atoms and 1, 2, 3 or 4 N, O and/or S atoms, which may be unsubstituted or mono-, di- or trisubstituted by Hal, A, CN, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$,
Het$^2$ denotes a monocyclic saturated heterocycle having 2, 3, 4, 5, 6 or 7 C atoms and 1, 2, 3 or 4 N, O and/or S atoms, which may be unsubstituted or monosubstituted by A,
Hal denotes F, Cl, Br or I,
m denotes 0, 1, 2, 3 or 4, and
n, p, s, independently of one another, denote 0, 1, 2, 3, 4, 5 or 6,
and/or physiologically acceptable salts, tautomers and/or stereoisomers thereof, including mixtures thereof in all ratios.

Surprisingly, it has been found that the compounds according to the invention are provided with inhibiting properties for serine/threonine protein kinases. The compounds of the formula (I) are designed in such a way, through their core structure of 2,3-dihydro-1H-imidazo-[4,5-c]quinoline, to which at least one alkoxy substitution, preferably a methoxy substitution, and an optionally substituted phenyl are attached, that potent and selective inhibition of DNA-PK occurs. The compounds according to the invention thus open up entirely new possibilities with respect to the anticarcinogenic action of anticancer agents. Remarkably, the compounds of the formula (I) play a therapeutic role as radio- and chemosensitisers in the treatment of cancer.

To date, it is merely known from WO 1992/07844 that 2,4-diaminoquinazoline derivatives are enhancers of chemotherapeutic agents in the treatment of cancer. The derivatives address the multiple resistance of tumour cells as a consequence of overexpression of the mdr1 gene, whose gene product of an efflux P glycoprotein pump keeps the intracellular active-compound concentration low. Inhibitors of phosphatidylinositol 3-kinase are also described generically in WO 2009/155527, which have neither the specific structure of formula (I) according to the invention nor the alkoxy substitution. Neither of the two prior-art documents discloses physicochemical or pharmacological data. A marketed medicament is equally unknown. By contrast, the present invention reveals that specifically compounds of the formula (I) are capable of the specific inhibition of serine/threonine protein kinases, such as DNA-PK. The compounds according to the invention and salts thereof consequently have valuable pharmacological properties while at the same time being well tolerated.

For the purposes of the invention, the compounds of the formula (I) are defined in such a way that they are also taken to mean pharmaceutically usable derivatives, salts, hydrates, solvates, precursors of the compounds, tautomers and optically active forms (such as, for example, stereoisomers, diastereomers, enantiomers, racemates). Solvates of the compounds are taken to mean adductions of inert solvent molecules onto the compounds, which form owing to their mutual attractive force. Solvates are, for example, mono- or di-hydrates or alcoholates. Pharmaceutically usable derivatives are taken to mean, for example, the salts of the compounds according to the invention and so-called precursors of the compounds. Precursors are taken to mean, for example, compounds of the formula (I) modified by means of alkyl or acyl groups, sugars or oligopeptides, which are rapidly cleaved in the organism to give the effective compounds according to the invention. These also include biodegradable polymer derivatives of the compounds according to the invention, as described, for example, in Int. J. Pharm. 115, 61-67 (1995). Any compound which can be converted in vivo into a bioactive agent, i.e. compounds of the formula (I), is a precursor in the sense of this invention. Any biologically active compound which results from the in-vivo metabolisation of a compound according to the invention is a metabolite in the sense of the present invention. The compounds of the formula (I) can have one or more chiral centres and therefore occur in various stereoisomeric forms. The formula (I) encompasses all these forms.

The invention also relates to the use of mixtures of the compounds of the formula (I), for example mixtures of two diastereomers, for example in the ratio 1:1, 1:2, 1:3, 1:4, 1:5, 1:10, 1:100 or 1:1000. Particular preference is given here to mixtures of stereoisomeric compounds.

Above and below, the radicals R1, R2, R3, R4, R5, R6, R7, X, Y, A, Alk, Ar, Het$^1$, Het$^2$ and Hal as well as m, n, p and s have the meanings indicated for the formula (I), unless expressly indicated otherwise. If individual radicals occur a number of times within a compound or radical, the radicals adopt, independently of one another, the meanings indicated, unless expressly indicated otherwise. For example, the radicals YY in the radical R4, in which they occur a number of times, are identical or different, but are preferably in each case selected, independently of one another, from the meanings indicated above and/or below (for example methyl and/or ethyl), unless expressly indicated otherwise. It likewise goes without saying, for example, that the index m in the notation $(R5)_m$ indicates the frequency of the substitution by the radical R5, i.e. the phenyl radical may carry up to 4 radicals R5 in different positions (but not a concatenation of up to 4 radicals in the same position), where the respective radicals R5 are selected, identically or differently, but preferably in each case independently of one another, from the meanings indicated above and/or below. In addition, the radicals R5 in the sub-formulae (IA) and (IB), in which they occur multiple times, are selected, identically or differently, but preferably in each case independently of one another, from the meanings indicated above and/or below (for example A and/or Hal). If R5 occurs multiple times, the radical may alternatively also be denoted by R5', R5'', R5''' and R5''''. The terms used here for the definition of the compounds are generally based on the rules of the IUPAC organisation for chemical compounds and in particular organic compounds. The terms for explanation of the above-mentioned compounds of the invention always have the following meanings, unless indicated otherwise in the description or claims.

The term "unsubstituted" means that a radical, a group or a residue carries no substituents. The term "substituted" means that a radical, a group or a residue carries one or more substituents.

"Alkyl" or "A" in the sense of the invention denotes a saturated or unsaturated hydrocarbon radical, which is unbranched (linear), branched or cyclic and preferably has 1, 2, 3, 4, 5, 6, 7, 8, 9 or 10 C atoms, i.e. $C_{1-10}$-alkanyl. Examples of alkyl radicals are methyl, ethyl, propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, pentyl, isopentyl, neopentyl, tert-pentyl, 1-, 2-, 3- or 4-methylpentyl, hexyl.

In a preferred embodiment of the invention, "A" is unbranched or branched alkyl having 1, 2, 3, 4, 5, 6, 7, 8, 9 or 10 C atoms, where, independently of one another, 1, 2, 3, 4, 5, 6 or 7 H atoms may be replaced by Hal. "A" is particularly preferably unbranched or branched alkyl having 1, 2, 3, 4, 5 or 6 C atoms, where 1, 2, 3, 4 or 5 H atoms may be replaced, independently of one another, by Hal. Very particular preference is given to $C_{1-4}$-alkyl, where, independently of one another, 1-3 H atoms may be replaced by Hal. A $C_{1-4}$-alkyl of this type is, for example, methyl, ethyl, propyl, isopropyl, butyl, isobutyl, sec-butyl, tert-butyl, fluoromethyl, difluoromethyl, trifluoromethyl, pentafluoroethyl, 1,1,1-trifluoroethyl or bromomethyl, most preferably methyl, ethyl or trifluoromethyl. It goes without saying that the respective meanings of "A" are independent of one another in the radicals of a formula according to the invention.

The term "Alk" in the sense of the invention denotes unbranched or branched alkylene, alkenyl or alkynyl having 1, 2, 3, 4, 5 or 6 C atoms, i.e. $C_{1-6}$-alkylenes, $C_{2-6}$-alkenyls and $C_{2-6}$-alkynyls. Alkenyls have at least one C—C double bond and alkynyls have at least one C—C triple bond. Alkynyls may in addition have at least one C—C double bond. Examples of suitable alkylenes are methylene, ethylene, propylene, butylene, pentylene, hexylene, isopropylene, isobutylene, sec-butylene, 1-, 2- or 3-methylbutylene, 1,1-, 1,2- or 2,2-dimethylpropylene, 1-ethylpropylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene. Examples of suitable alkenyls are allyl, vinyl, propenyl (—CH$_2$CH═CH$_2$; —CH═CH—CH$_3$; —O(═OH$_2$)—OH$_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl. Examples of suitable alkynyls are ethynyl, propynyl (—CH$_2$—C≡CH; —C≡C—CH$_3$), 1-, 2- or 3-butynyl, pentynyl, hexynyl or pent-3-en-1-ynyl, in particular propynyl.

In a preferred embodiment of the invention, "Alk" is alkenyl having 1-6 C atoms, i.e. methenyl, ethenyl, propenyl, butenyl, pentenyl or hexenyl, where 1-4 H atoms may be replaced, independently of one another, by Hal and/or OY. It is particularly preferred for "Alk" to denote alkenyl having 1-3 C atoms, where 1-2 H atoms may be replaced by Hal and/or OH. Very particularly preferred examples thereof are methenyl, ethenyl and propenyl. It goes without saying that the respective meanings of "Alk" are independent of one another in the radicals of a formula according to the invention.

Skeleton of the formula (I) is any generic or non-generic structure to which any radical in the sense of the invention, such as, for example. Ar, Het$^1$ or Het$^2$, can be bonded in order to obtain a compound of the formula (I) according to the invention.

The term "aryl", "carboaryl" or "Ar" in the sense of the invention denotes a mono- or poly-cyclic aromatic hydrocarbon system having 3, 4, 5, 6, 7, 8, 9, 10, 11, 12, 13 or 14, preferably 4-10, particularly preferably 5-8, C atoms, which may optionally be substituted. The term "aryl" includes systems in which the aromatic ring is part of a bi- or polycyclic saturated, partially unsaturated and/or aromatic system, for example if the aromatic ring is fused to "aryl", "heteroaryl" or "heterocyclyl" via any desired ring member of the aryl radical. The bonding to the basic structure of the formula (I) can take place via any ring member of the aryl group. Examples of suitable "aryl" are phenyl, biphenyl, naphthyl, 1-naphthyl, 2-naphthyl, anthracenyl, indanyl, indenyl, 1,2,3,4-tetrahydronaphthyl, in particular phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

In a preferred embodiment of the invention, "Ar" is phenyl which is unsubstituted or mono, di- or trisubstituted by Hal, A, CN, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY. It is particularly preferred for "Ar" to denote phenyl which is unsubstituted or mono- or disubstituted by Hal. It goes without saying that the respective meanings of "Ar" are independent of one another in the radicals of a formula according to the invention.

The term "heteroaryl" in the sense of the invention denotes a 2, 3, 4, 5, 6, 7, 8, 9, 10, 11, 12, 13, 14 or 15, preferably 2-9, particularly preferably 5-, 6- or 7-membered mono- or poly-cyclic aromatic hydrocarbon radical which contains at least 1, if appropriate also 2, 3, 4 or 5 heteroatoms, in particular nitrogen, oxygen and/or sulfur, where the heteroatoms are identical or different. The number of nitrogen atoms is preferably 0, 1, 2, 3 or 4, and the number of oxygen and sulfur atoms is, independently of one another, 0 or 1. The term "heteroaryl" includes systems in which the aromatic ring is part of a bi- or polycyclic saturated, partially unsaturated and/or aromatic system, for example if the aromatic ring is fused to "aryl", "heteroaryl" or "heterocyclyl" via any desired ring member of the heteroaryl radical. The bonding to the basic structure of the formula (I) can take place via any ring member of the heteroaryl group, so long as it appears chemically sensible, where bonding via the C atoms is preferred.

"Heteroaryl" denotes, irrespective of further substitutions, for example 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, 1,3-benzodioxol-5-yl, 1,4-benzodioxan-6-yl, 2,1,3-benzothiadiazol-4- or -5-yl, 2,1,3-benzoxadiazol-5-yl, imidazolyl, triazinyl, phthalazinyl, indolizinyl, pteridinyl, carbazolyl, phenazinyl, phenoxazinyl, phenothiazinyl or acridinyl.

The heterocyclic radicals may also be partially or fully hydrogenated. Unsubstituted heteroaryl may thus, for example, also denote 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl, or also 3,4-dihydro-2H-1,5-benzodioxepin-6- or -7-yl, 2,3-dihydrobenzofuranyl or 2,3-dihydro-2-oxofuranyl.

It is preferred for "heteroaryl" in the sense of "Het$^1$" to denote a mono- or bicyclic aromatic heterocycle having 2, 3, 4, 5, 6, 7, 8 or 9 C atoms and 1, 2, 3 or 4 N, O and/or S atoms, which may be unsubstituted or mono- di- or trisubstituted by Hal, A, CN, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$. It is particularly preferred for "Het$^1$" to denote mono- or bicyclic heteroaryl having 2, 3, 4, 5, 6, 7, 8 or 9 C atoms and 1, 2 or 3 N and/or S atoms, which may be unsubstituted or mono- or disubstituted by Hal, A, OY or —SO$_2$-Het$^2$. It goes without saying that the respective meanings of "Het$^1$" are independent of one another in the radicals of a formula according to the invention.

The term "heterocycle" in the sense of the invention denotes a mono- or polycyclic system having 3, 4, 5, 6, 7, 8, 9, 10, 11, 12, 13, 14, 15, 16, 17, 18, 19 or 20 ring atoms, preferably 3-14 ring atoms, particularly preferably 3-10 ring atoms, comprising C atoms and 1, 2, 3, 4 or 5 heteroatoms, in particular nitrogen, oxygen and/or sulfur, where the heteroatoms are identical or different. The cyclic system may be saturated or mono- or polyunsaturated. The term "heteroaryl" includes systems in which the aromatic ring is part of a bi- or polycyclic saturated, partially unsaturated and/or aromatic system, for example if the aromatic ring is fused to "aryl", "heteroaryl" or "heterocyclyl" via any desired ring member of the heterocycle. The bonding to the basic structure of the formula (I) can take place via any ring member of the heterocycle. Examples of suitable heterocycles are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In an embodiment of the invention, "Het$^2$" is a monocyclic saturated heterocycle having 2, 3, 4, 5, 6 or 7 C atoms and 1, 2, 3 or 4 N, O and/or S atoms, which may be unsubstituted or monosubstituted by A. It is preferred for "Het$^2$" to denote a monocyclic saturated heterocycle having 3, 4 or 5 C atoms and 1 or 2 N and/or O atoms.

The term "halogen", "halogen atom", "halogen substituent" or "Hal" in the sense of the invention denotes one or more atoms of fluorine (F), bromine (Br), chlorine (Cl) or iodine (I). The terms "dihalogen", "trihalogen" and "perhalogen" relate to two, three or four substituents, where each substituent can be selected, independently of one another, from the group of F, Cl, Br or I. "Halogen" preferably means F, Cl or Br. F and Cl are particularly preferred, in particular if the halogens are substituted on an alkyl (haloalkyl) or alkoxy group (for example CF$_3$ and CF$_3$O).

The radical R1 preferably denotes H or A, particularly preferably A.

The radical R2 preferably denotes H, A, —(CY$_2$)$_p$—C(YR6)-R7, R7, -Alk-Ar or -Alk-Het$^1$, particularly preferably H, A, —CH(R6)-R7, Het$^1$ or -Alk-Het$^1$.

The radical R3 preferably denotes H or CN, particularly preferably CN.

The radical R4 preferably denotes H or A, particularly preferably A.

The radical R5 preferably denotes Y or Hal, particularly preferably H or Hal, very particularly preferably Hal.

The radical R6 preferably denotes Y, —(CY$_2$)$_n$—NYY, —CO—NYY or —CO—NY—(CY$_2$)$_n$—OY, particularly preferably H, —CH$_2$—NH$_2$, —CO—NH$_2$ or —CO—NH—(CH$_2$)$_n$—OA, very particularly preferably H.

The radical R7 preferably denotes Ar or Het$^1$.

The radical X preferably denotes O or a single bond.

The index m preferably denotes 0, 1 or 2, particularly preferably 1 or 2.

The index n preferably denotes 0, 1, 2 or 3, particularly preferably 1 or 2.

The index p preferably denotes 0, 1, 2 or 3, particularly preferably 0.

The index s preferably denotes 0, 1, 2 or 3, particularly preferably 0 or 1.

Accordingly, the invention relates to the compounds of the formula (I) in which at least one of the said radicals has one of the meanings indicated above. Radicals which are not denoted in greater detail in the context of an embodiment of the formula (I), part-formula thereof or any residue thereon are intended to have the meaning indicated for the formula (I), as disclosed herein, in order to achieve the object of the invention. This means that the said radicals may adopt all meanings assigned to them, as described above or below, including any preferred embodiments, without being restricted thereto and independently of their occurrence in another particular context. It goes without saying, in particular, that each embodiment of a certain radical can be combined with each embodiment of one or more other radicals.

In a preferred embodiment of the present invention, imidazolonylquinoline derivatives of the sub-formula (IA) are provided

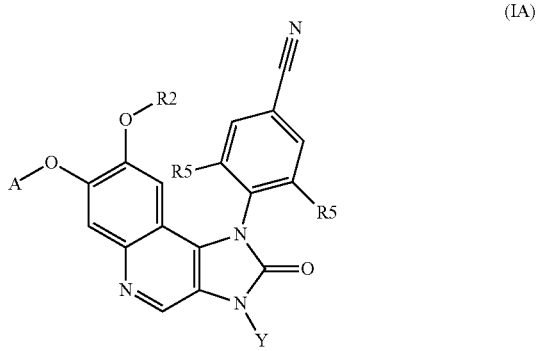

(IA)

in which
R2 denotes Y or —(CY$_2$)$_p$—C(YR6)-R7,
R5 denotes Y or Hal,
R6 denotes Y, —(CY$_2$)$_n$—NYY, —CO—NYY or —CO—NY—(CY$_2$)$_n$—OY,
R7 denotes Ar or Het$^1$,
Y denotes H or A,
A denotes unbranched or branched alkyl having 1, 2, 3 or 4 C atoms, where 1, 2 or 3 H atoms may be replaced, independently of one another, by Hal,
Ar denotes phenyl which is unsubstituted or mono- or disubstituted by Hal,
Het$^1$ denotes mono- or bicyclic heteroaryl having 2, 3, 4, 5, 6, 7, 8 or 9 C atoms and 1, 2 or 3 N and/or S atoms, which may be unsubstituted or mono- or disubstituted by Hal, A, OY or —SO$_2$-Het$^2$,
Het$^2$ denotes a monocyclic saturated heterocycle having 3, 4 or 5 C atoms and 1 or 2 N and/or O atoms,
Hal denotes F, Cl, Br or I, and
n, p, independently of one another, denote 0, 1, 2 or 3,
and/or physiologically acceptable salts, tautomers and/or stereoisomers thereof, including mixtures thereof in all ratios.

In another preferred embodiment of the present invention, imidazolonylquinoline derivatives of the sub-formula (IB) are provided

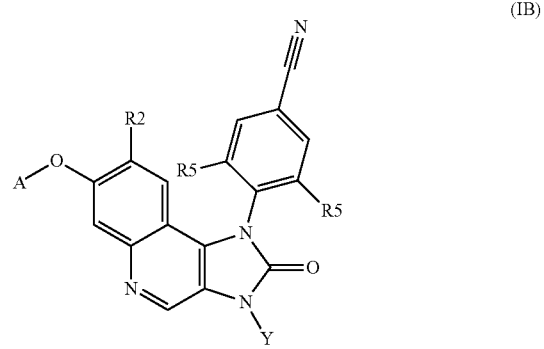

(IB)

in which
R2 denotes R7, -alk-Ar or -alk-Het$^1$,
R5 denotes Y or Hal,
R7 denotes —(CY$_2$)$_p$—Ar or —(CY$_2$)$_p$-Het$^1$,
Y denotes H or A,
A denotes unbranched or branched alkyl having 1, 2, 3 or 4 C atoms, where 1, 2 or 3 H atoms may be replaced, independently of one another, by Hal,
Alk denotes alkenyl having 1, 2 or 3 C atoms, where 1 or 2 H atoms may be replaced by Hal and/or OH,
Ar denotes phenyl which is unsubstituted or mono- or disubstituted by Hal,
Het$^1$ denotes mono- or bicyclic heteroaryl having 2, 3, 4, 5, 6, 7, 8 or 9 C atoms and 1, 2 or 3 N and/or S atoms, which may be unsubstituted or mono- or disubstituted by Hal, A, OY or —SO$_2$-Het$^2$,
Het$^2$ denotes a monocyclic saturated heterocycle having 3, 4 or 5 C atoms and 1 or 2 N and/or O atoms,
Hal denotes F, Cl, Br or I, and
p, independently of one another, denotes 0, 1, 2 or 3,
and/or physiologically acceptable salts, tautomers and/or stereoisomers thereof, including mixtures thereof in all ratios.

In a particularly preferred embodiment of the present invention, imidazolonylquinoline derivatives of the sub-formula (IB-1) are provided

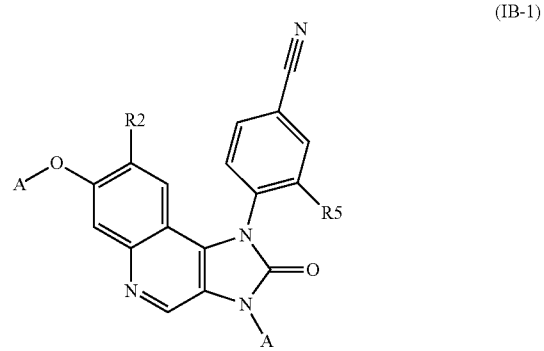

(IB-1)

in which
R2 denotes R7, -alk-Ar or -alk-Het$^1$,
R5 denotes Hal,
R7 denotes Ar or Het$^1$,
A denotes unbranched or branched alkyl having 1, 2, 3 or 4 C atoms, where 1, 2 or 3 H atoms may be replaced, independently of one another, by Hal, Alk denotes alkenyl having 1 or 2 C atoms,
Ar denotes phenyl which is unsubstituted or monosubstituted by Hal,
Het¹ denotes mono- or bicyclic heteroaryl having 2, 3, 4, 5, 6, 7, 8 or 9 C atoms and 1, 2 or 3 N and/or S atoms, which may be unsubstituted or mono- or disubstituted by Hal or A or, and Hal denotes F, Cl, Br or I,
and/or physiologically acceptable salts, tautomers and/or stereoisomers thereof, including mixtures thereof in all ratios.

Very particular preference is given to compounds of the formulae (I), (IA), (IB) and (IB-1) which are compiled in Table 1.

TABLE 1

Very particularly preferred compounds of the formulae (I), (IA), (IB) and (IB-1) and/or physiologically acceptable salts, tautomers and/or stereoisomers thereof, including mixtures thereof in all ratios 1 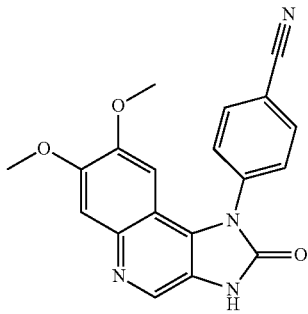 [SMILES: COc1cc2ncc3[nH]c(=O)n(-c4ccc(C#N)cc4)c3c2cc1OC]

2 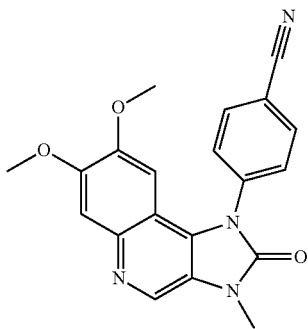 [SMILES: COc1cc2ncc3c(c2cc1OC)n(-c1ccc(C#N)cc1)c(=O)n3C]

3 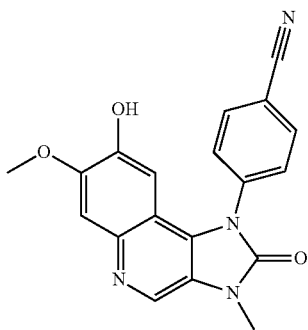 [SMILES: COc1cc2ncc3c(c2cc1O)n(-c1ccc(C#N)cc1)c(=O)n3C]

4 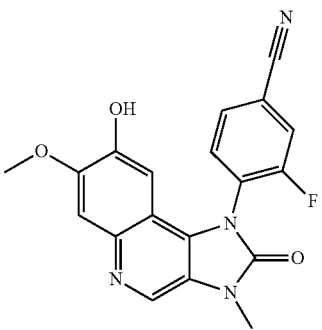 [SMILES: COc1cc2ncc3c(c2cc1O)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
5 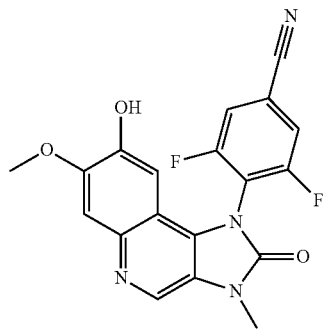 [SMILES: COc1cc2ncc3c(c2cc1O)n(-c1c(F)cc(C#N)cc1F)c(=O)n3C]
6 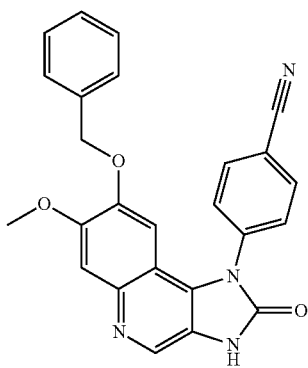 [SMILES: COc1cc2ncc3[nH]c(=O)n(-c4ccc(C#N)cc4)c3c2cc1OCc1ccccc1]
7 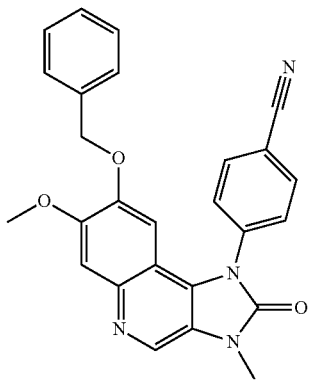 [SMILES: COc1cc2ncc3c(c2cc1OCc1ccccc1)n(-c1ccc(C#N)cc1)c(=O)n3C]
8 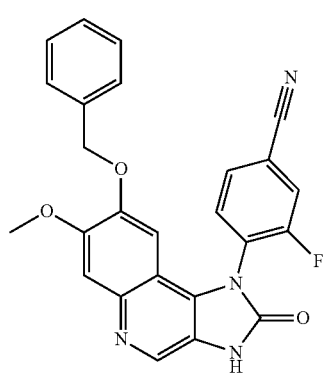 [SMILES: COc1cc2ncc3[nH]c(=O)n(-c4ccc(C#N)cc4F)c3c2cc1OCc1ccccc1]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
9
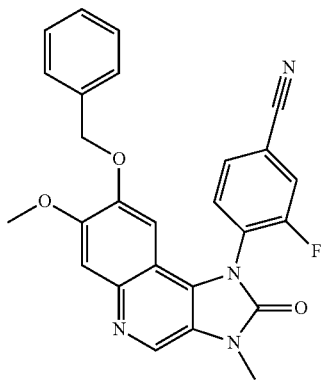 [SMILES: COc1cc2ncc3c(c2cc1OCc1ccccc1)n(-c1ccc(C#N)cc1F)c(=O)n3C]
10
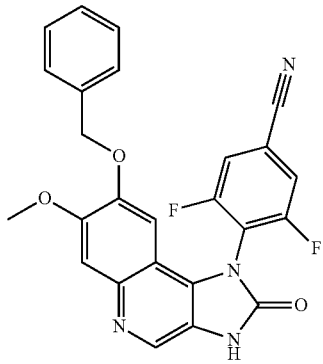 [SMILES: COc1cc2ncc3[nH]c(=O)n(-c4c(F)cc(C#N)cc4F)c3c2cc1OCc1ccccc1]
11
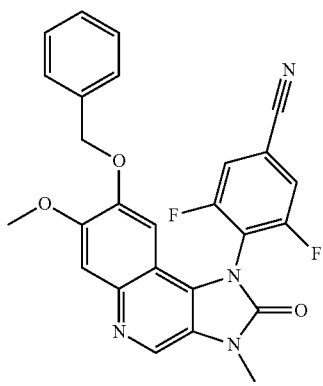 [SMILES: COc1cc2ncc3c(c2cc1OCc1ccccc1)n(-c1c(F)cc(C#N)cc1F)c(=O)n3C]

TABLE 1-continued
Very particularly preferred compounds of the formulae (I), (IA), (IB) and (IB-1)
and/or physiologically acceptable salts, tautomers and/or stereoisomers thereof, including
mixtures thereof in all ratios
12 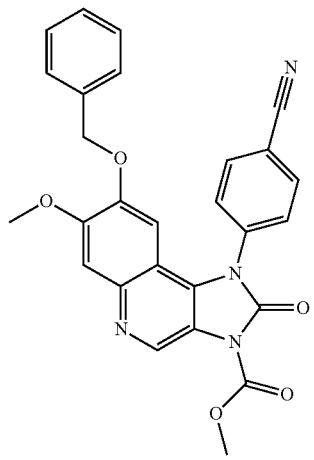 [SMILES: COC(=O)n1c(=O)n(-c2ccc(C#N)cc2)c2c3cc(OCc4ccccc4)c(OC)cc3ncc21]
13 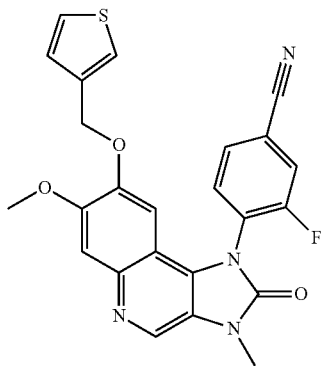 [SMILES: COc1cc2ncc3c(c2cc1OCc1ccsc1)n(-c1ccc(C#N)cc1F)c(=O)n3C]
14 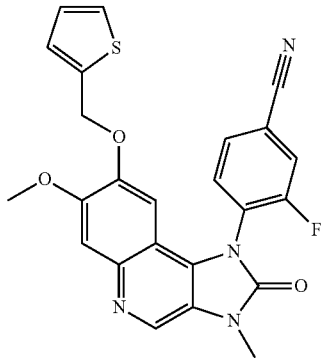 [SMILES: COc1cc2ncc3c(c2cc1OCc1cccs1)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
15
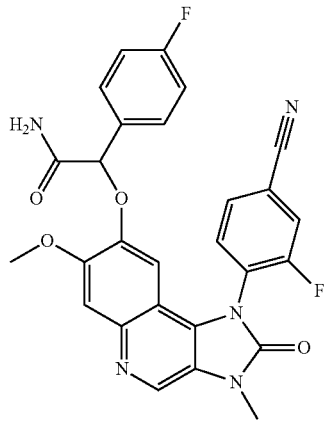 [SMILES: COc1cc2ncc3c(c2cc1OC(C(N)=O)c1ccc(F)cc1)n(-c1ccc(C#N)cc1F)c(=O)n3C]
16
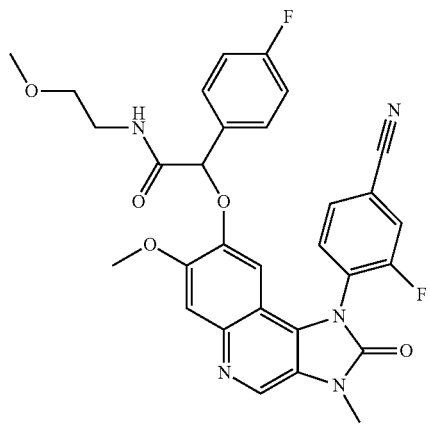 [SMILES: COCCNC(=O)C(Oc1cc2c(cc1OC)ncc1c2n(-c2ccc(C#N)cc2F)c(=O)n1C)c1ccc(F)cc1]
17
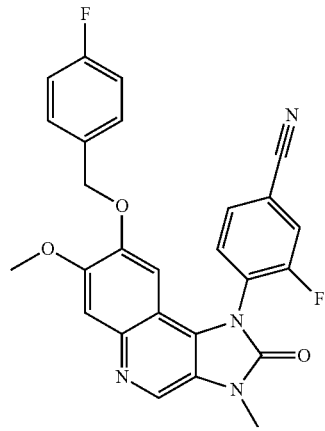 [SMILES: COc1cc2ncc3c(c2cc1OCc1ccc(F)cc1)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
18 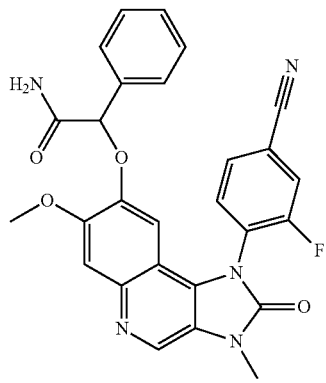 [SMILES: COc1cc2ncc3c(c2cc1OC(C(N)=O)c1ccccc1)n(-c1ccc(C#N)cc1F)c(=O)n3C]
19 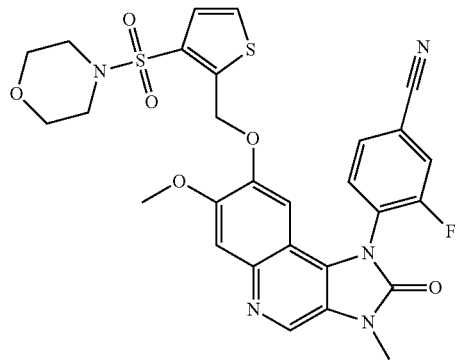 [SMILES: COc1cc2ncc3c(c2cc1OCc1sccc1S(=O)(=O)N1CCOCC1)n(-c1ccc(C#N)cc1F)c(=O)n3C]
20 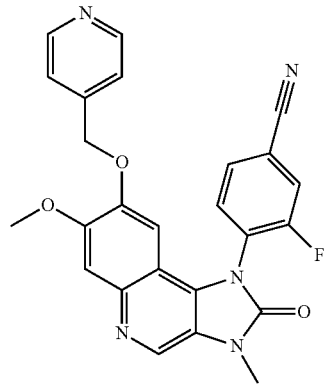 [SMILES: COc1cc2ncc3c(c2cc1OCc1ccncc1)n(-c1ccc(C#N)cc1F)c(=O)n3C]
21 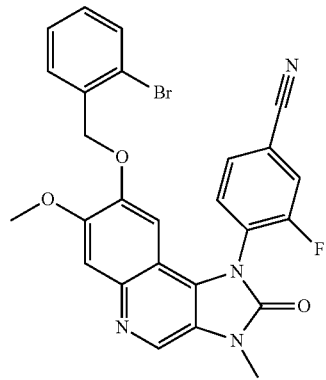 [SMILES: COc1cc2ncc3c(c2cc1OCc1ccccc1Br)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
22 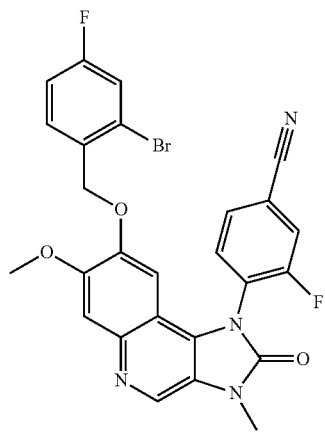
23 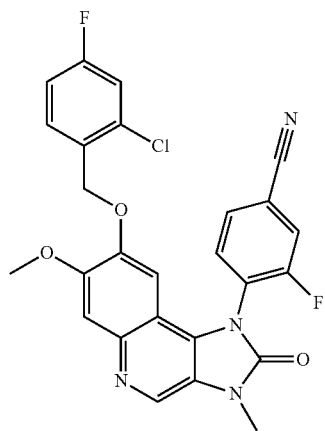
24 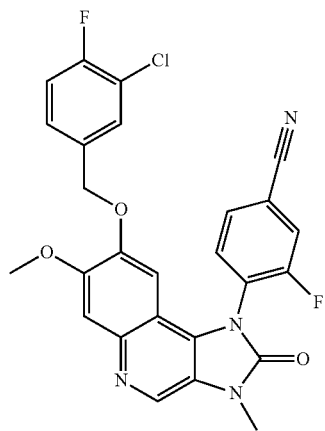 [SMILES: COc1cc2ncc3c(c2cc1OCc1ccc(F)c(Cl)c1)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
25 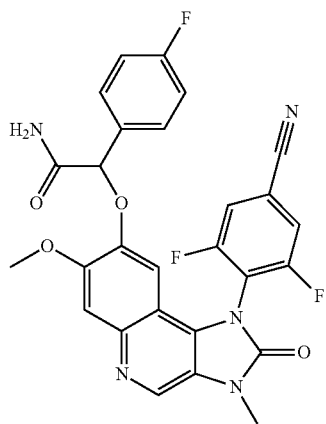 [SMILES: COc1cc2ncc3c(c2cc1OC(C(N)=O)c1ccc(F)cc1)n(-c1c(F)cc(C#N)cc1F)c(=O)n3C]
26 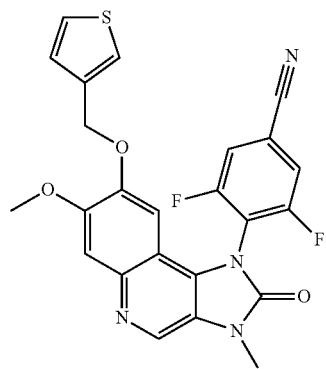 [SMILES: COc1cc2ncc3c(c2cc1OCc1ccsc1)n(-c1c(F)cc(C#N)cc1F)c(=O)n3C]
27 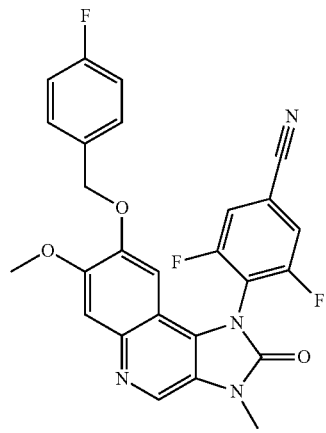 [SMILES: COc1cc2ncc3c(c2cc1OCc1ccc(F)cc1)n(-c1c(F)cc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
28
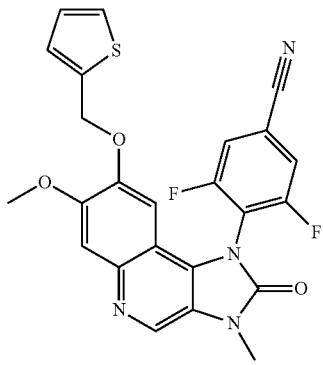 [SMILES: COc1cc2ncc3c(c2cc1OCc1cccs1)n(-c1c(F)cc(C#N)cc1F)c(=O)n3C]
29
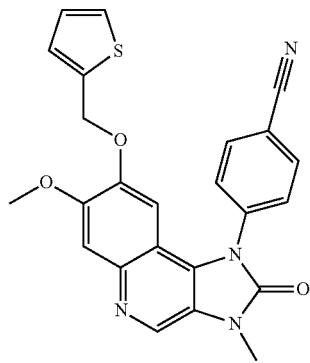 [SMILES: COc1cc2ncc3c(c2cc1OCc1cccs1)n(-c1ccc(C#N)cc1)c(=O)n3C]
30
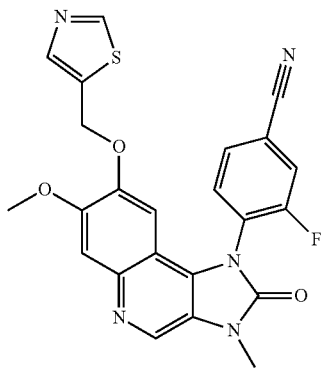 [SMILES: COc1cc2ncc3c(c2cc1OCc1cncs1)n(-c1ccc(C#N)cc1F)c(=O)n3C]
31
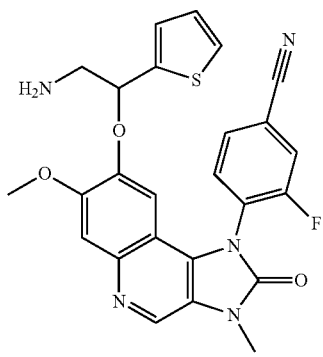 [SMILES: COc1cc2ncc3c(c2cc1OC(CN)c1cccs1)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
32
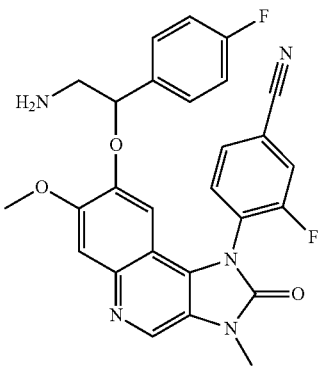 [SMILES: COc1cc2ncc3c(c2cc1OC(CN)c1ccc(F)cc1)n(-c1ccc(C#N)cc1F)c(=O)n3C]
33
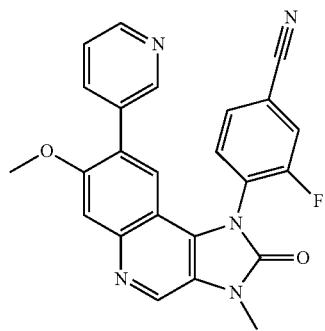 [SMILES: COc1cc2ncc3c(c2cc1-c1cccnc1)n(-c1ccc(C#N)cc1F)c(=O)n3C]
34
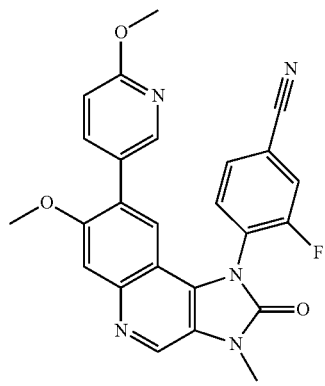 [SMILES: COc1ccc(-c2cc3c(cc2OC)ncc2c3n(-c3ccc(C#N)cc3F)c(=O)n2C)cn1]
35
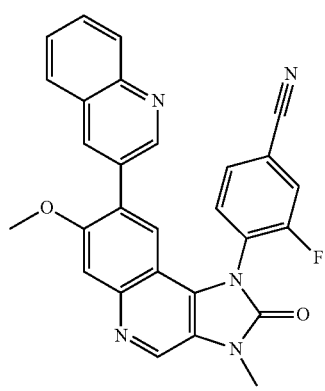 [SMILES: COc1cc2ncc3c(c2cc1-c1cnc2ccccc2c1)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
36 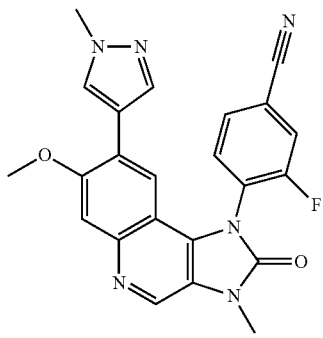 [SMILES: COc1cc2ncc3c(c2cc1-c1cnn(C)c1)n(-c1ccc(C#N)cc1F)c(=O)n3C]
37 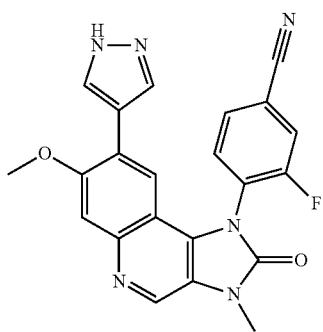 [SMILES: COc1cc2ncc3c(c2cc1-c1cn[nH]c1)n(-c1ccc(C#N)cc1F)c(=O)n3C]
38 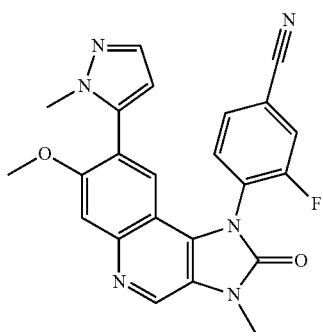 [SMILES: COc1cc2ncc3c(c2cc1-c1ccnn1C)n(-c1ccc(C#N)cc1F)c(=O)n3C]
39 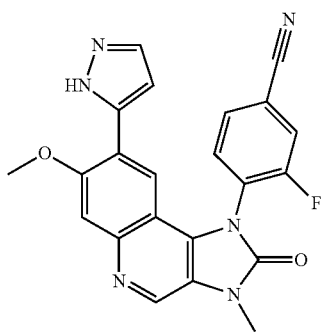 [SMILES: COc1cc2ncc3c(c2cc1-c1ccn[nH]1)n(-c1ccc(C#N)cc1F)c(=O)n3C]

TABLE 1-continued
Very particularly preferred compounds of the formulae (I), (IA), (IB) and (IB-1) and/or physiologically acceptable salts, tautomers and/or stereoisomers thereof, including mixtures thereof in all ratios
40 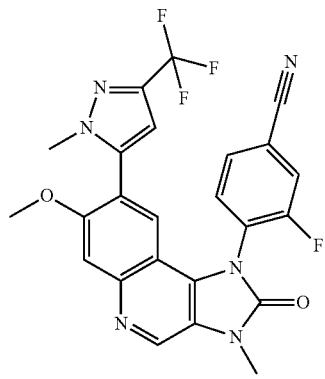 [SMILES: COc1cc2ncc3c(c2cc1-c1cc(C(F)(F)F)nn1C)n(-c1ccc(C#N)cc1F)c(=O)n3C]
41 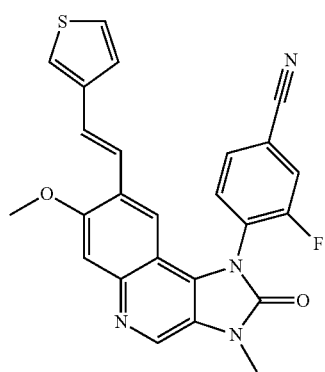 [SMILES: COc1cc2ncc3c(c2cc1/C=C/c1ccsc1)n(-c1ccc(C#N)cc1F)c(=O)n3C]
42 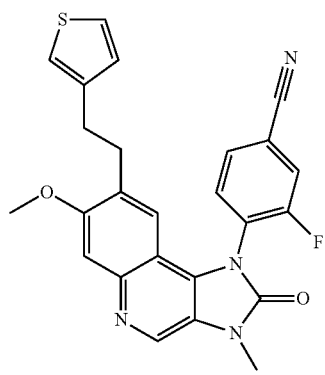 [SMILES: COc1cc2ncc3c(c2cc1CCc1ccsc1)n(-c1ccc(C#N)cc1F)c(=O)n3C]
43 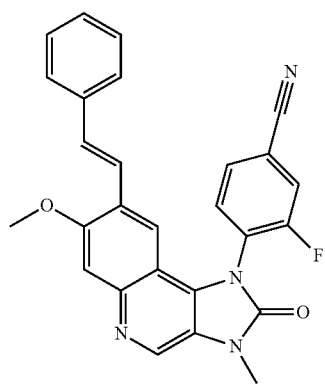 [SMILES: COc1cc2ncc3c(c2cc1/C=C/c1ccccc1)n(-c1ccc(C#N)cc1F)c(=O)n3C]

The compounds of the formula (I) and also the starting materials for their preparation are prepared by methods known per se, as are described in the literature (for example in standard works, such as Houben-Weyl, Methoden der organischen Chemie [Methods of Organic Chemistry], Georg-Thieme-Verlag, Stuttgart) and/or are known person skilled in the art, and under reaction conditions which are known and suitable for the said reactions. Use can also be made here of variants known per se which are not mentioned here in greater detail.

Depending on the conditions used, the reaction time is between a few minutes and 14 days, the reaction temperature is between −15° C. and 150° C., normally between 10° C. and 100° C., particularly preferably between 20° C. and 70° C.

The reaction is carried out in an inert solvent and generally in the presence of an acid-binding agent, preferably an organic base, such as DIPEA, triethylamine, dimethylaniline, pyridine, quinoline, piperidine or diethanolamine. The addition of an alkali-metal or alkaline-earth metal hydroxide, carbonate or bicarbonate or another salt of a weak acid of the alkali or alkaline-earth metals, preferably of potassium, sodium, calcium or caesium, may also be favourable. Suitable bases are metal oxides, such as, for example, aluminium oxide, alkali-metal hydroxides (including potassium hydroxide, sodium hydroxide and lithium hydroxide), alkaline-earth metal hydroxides (for example barium hydroxide and calcium hydroxide) and alkali-metal alkoxides (for example potassium ethoxide and sodium propoxide).

Suitable inert solvents are, inter alia, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to glycol ethers, such as ethylene glycol monomethyl ether, THF, dichloromethane and/or DMF.

The process and the subsequent work-up of the reaction mixture can basically be carried out as a batch reaction or in a continuous reaction procedure. The continuous reaction procedure comprises, for example, reaction in a continuous stirred-kettle reactor, a stirred-kettle cascade, a loop or cross-flow reactor, a flow tube or in a microreactor. The reaction mixtures are optionally worked up, as needed, by filtration via solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

The compounds of the formula (I) can preferably be obtained by reacting a compound of the formula (II). The present invention thus also relates to a process for the preparation of compounds of the formula (I), part-formulae thereof and/or physiologically acceptable salts, tautomers and/or stereoisomers thereof, including mixtures thereof in all ratios, having the following steps:

(a) reaction of a compound of the formula (II)

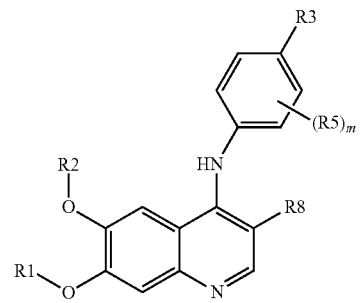

(II)

in which
R1 denotes A,
R2 denotes A or —(CH$_2$)$_p$—(CH$_2$)$_s$—Ar,
R3 denotes CN,
R5 denotes Hal,
R8 denotes NH$_2$,
A denotes unbranched or branched alkyl having 1, 2, 3 or 4 C atoms, where 1, 2 or 3 H atoms may be replaced, independently of one another, by Hal,
Ar denotes phenyl which is unsubstituted or mono- or disubstituted by Hal,
Hal denotes F, Cl, Br or I, and
m, p, s, independently of one another, denote 0, 1 or 2,
preferably in which
R8 denotes NO$_2$ or NYY, particularly preferably NYY, and
R1, R2, R3, R5, R6, R7, Y, A, Alk, Ar, Het1, Het$^2$ and Hal as well as m, n, p and s have the meaning indicated above in formula (I),
with a carboxylic acid halide and with an organic base, preferably Hünig's base, in a solvent,
to give compounds of the sub-formula (IC)

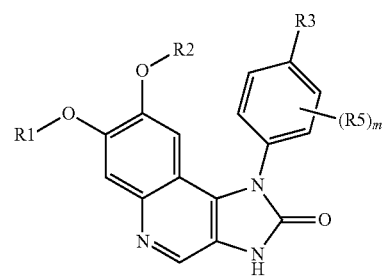

(IC)

in which R1, R2, R3, R5 and m have the meaning indicated above in formula (II),
and optionally
(b') reaction of the compounds of the sub-formula (IC) with a compound Hal-R4, in which R4 and Hal have the meaning indicated above,
to give compounds of the sub-formula (ID)

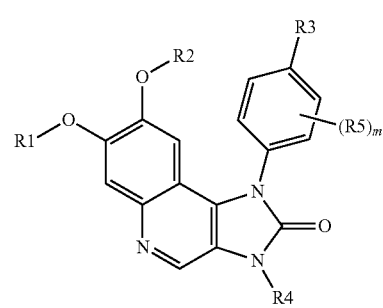

(ID)

in which R1, R2, R3, R5 and m have the the meaning indicated above in formula (II), and R4 has the meaning indicated above, (b″) conversion of R1, —O—R2, R3, R4 and/or R5 of the compounds of the sub-formula (ID) and/or addition of at least one R5 having the meaning indicated above to the phenyl ring of the compounds of the sub-formula (ID) to give compounds of the formula (I)

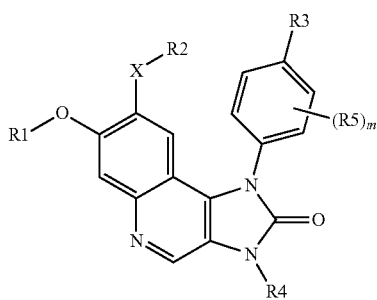

(I)

in which R1, R2, R3, R4, R5, X and m have the meaning indicated above,
and/or (b‴) conversion of a base or acid of the compounds of the formula (I) or sub-formulae (IC) or (ID) into one of its physiologically acceptable salts.

For the purposes of the invention, it goes without saying here that a radical can adopt all meanings given previously in the description for the corresponding radical by reference to "the meaning indicated above" without more detailed specification thereof.

The invention also relates to intermediate compounds of the formula (II)

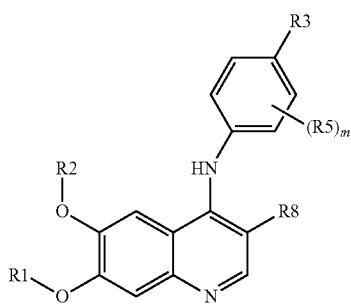

(II)

in which
R8 denotes NO$_2$ or NYY, and
R1, R2, R3, R5, Y and m have the meaning indicated above,
and/or salts, tautomers and/or stereoisomers thereof, including mixtures thereof in all ratios.

In a preferred embodiment of the present invention, intermediate compounds of the formula (II) are provided in which
R1 denotes A,
R2 denotes A or —(CH$_2$)$_p$—(CH$_2$)$_s$—Ar,
R3 denotes CN,
R5 denotes Hal,
R8 denotes NH$_2$,
A denotes unbranched or branched alkyl having 1, 2, 3 or 4 C atoms, where 1, 2 or 3 H atoms may be replaced, independently of one another, by Hal, Ar denotes phenyl which is unsubstituted or mono- or disubstituted by Hal,
Hal denotes F, Cl, Br or I, and
m, p, s, independently of one another, denote 0, 1 or 2,
and/or salts, tautomers and/or stereoisomers thereof, including mixtures thereof in all ratios.

The invention also relates to a process for the preparation of intermediate compounds of the formula (II) and/or salts, tautomers and/or stereoisomers thereof, including mixtures thereof in all ratios, having the following steps:
(a) reaction of a compound of the formula (III)

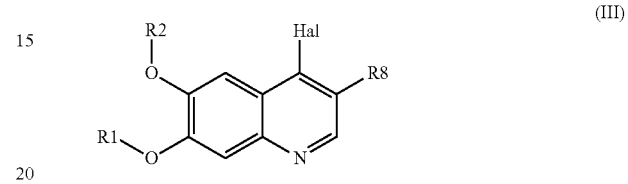

(III)

in which R1, R2, R8 and Hal have the meaning indicated above,
with a compound of the formula (IV)

(IV)

in which R3, R5 and m have the meaning indicated above, to give compounds of the formula (II)

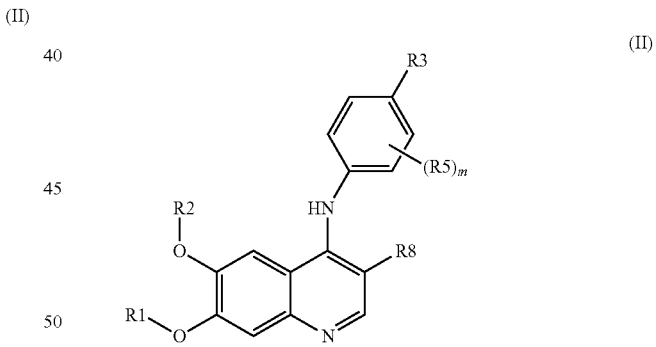

(II)

in which R1, R2, R3, R5, R8 and m have the meaning indicated above.
and optionally
(b) conversion of a base or acid of the compounds of the formula (II) into one of its salts.

The starting compounds are generally known. If they are novel, they can be prepared by methods known per se. The compounds of the formulae (III) and (IV) can be prepared by known methods. If desired, the starting materials can be formed in situ, so that they are not isolated from the reaction mixture, but instead are immediately converted further into the compounds according to the invention. It is likewise possible to carry out the reaction step-wise.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula (I) and part-formulae thereof are for the most part prepared by conventional methods. If the compounds contain a carboxyl group, one of its suitable salts can be formed by reacting the compound with a suitable base to give the corresponding base-addition salt. Such bases are, for example, alkali-metal hydroxides (for example potassium hydroxide, sodium hydroxide and lithium hydroxide), alkaline-earth metal hydroxides (for example barium hydroxide and calcium hydroxide), alkali-metal alkoxides (for example potassium ethoxide and sodium propoxide) and various organic bases, such as piperidine, diethanolamine and N-methylglutamine. A base of the formulae (I) and (II) and part-formulae thereof can be converted into the associated acid-addition salt using an acid, for example by reaction of equivalent amounts of the base and the acid in an inert solvent, such as, for example, ethanol, with subsequent evaporation. Suitable acids for this reaction are, in particular, those which give physiologically acceptable salts, such as, for example, hydrogen halides (for example hydrogen chloride, hydrogen bromide or hydrogen iodide), other mineral acids and corresponding salts thereof (for example sulfate, nitrate or phosphate and the like), alkyl- and mono-arylsulfonates (for example ethanesulfonate, toluenesulfonate and benzenesulfonate) and other organic acids and corresponding salts thereof (for example acetate, trifluoroacetate, tartrate, maleate, succinate, citrate, benzoate, salicylate, ascorbate and the like. Salts with physiologically unacceptable acids, for example picrates, can be used for the isolation and/or purification of the compounds of the formula (I).

With regard to that stated above, it can be seen that the expression "pharmaceutically acceptable salt" in the present connection is taken to mean an active compound which comprises a compound of the formula (I) in the form of one of its salts, in particular if this salt form imparts improved pharmacokinetic properties on the active compound compared with the free form of the active compound. The pharmaceutically acceptable salt form of the active compound can also provide this active compound for the first time with a desired pharmacokinetic property and can even have a positive influence on the pharmacodynamics of this active compound with respect to its therapeutic efficacy in the body.

Compounds according to the invention may be chiral owing to their molecular structure and may accordingly occur in various enantiomeric forms. They may therefore be in racemic or optically active form. Since the pharmaceutical efficacy of the racemates or stereoisomers of the compounds of the formula (I) may differ, it may be desirable to use the enantiomers. In these cases, the end product, or even the intermediate, may be separated into enantiomeric compounds by chemical or physical measures known to the person skilled in the art or already employed as such in the synthesis.

Surprisingly, it has been found that the compounds according to the invention cause specific inhibition of serine/threonine protein kinases. The invention therefore furthermore relates to the use of compounds of the formula (I) or part-formulae thereof and/or physiologically acceptable salts, tautomers and/or stereoisomers thereof, including mixtures thereof in all ratios, for the inhibition of serine/threonine protein kinases, preferably PIKK and/or ATM, particularly preferably DNA-PK. The term "inhibition" relates to any reduction in the activity which is based on the action of the specific compounds according to the invention in that the latter are capable of interacting with the target molecule in such a way that recognition, binding and blocking is made possible. The compounds are distinguished by high affinity to at least one serine/threonine protein kinases, ensuring reliable binding and preferably complete blocking of the kinase activity. The compounds are particularly preferably monospecific in order to guarantee exclusive and direct recognition of the selected kinase. The term "recognition" relates here to any type of interaction between the compound and the said target molecules, in particular covalent or non-covalent bonds, such as, for example, a covalent bond, hydrophobic/hydrophilic interactions, van der Waals forces, ion attraction, hydrogen bonds, ligand/receptor interactions, base pairs of nucleotides or interactions between epitope and antibody binding site.

The compounds according to the invention exhibit an advantageous biological activity which can be demonstrated in the tests described herein, such as, for example, enzyme-based assays. Measurement of the kinase activity is a technique which is well known to the person skilled in the art. Generic test systems for the determination of the kinase activity using substrates, for example histone (Alessi et al. (1996) FEBS Lett. 399(3): 333) or the basic myelin protein, are described in the literature (Campos-González & Glenney (1992) JBC 267: 14535). Various assay systems are available for the identification of kinase inhibitors. In the scintillation proximity assay (Sorg et al. (2002) J Biomolecular Screening 7: 11) and the flashplate assay, the radioactive phosphorylation of a protein or peptide as substrate are measured using ATP. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are useful as assay methods (Sills et al. (2002) J Biomolecular Screening 191). Other non-radioactive ELISA methods use specific phospho-antibodies (phospho-ABs). The phospho-AB binds only the phosphorylated substrate. This binding can be detected by chemiluminescence using a second peroxidase-conjugated anti-sheep antibody.

The above-mentioned use of the compounds can take place in in-vitro or in-vivo models. The susceptibility of a particular cell to treatment with the compounds according to the invention can be determined by testing in vitro. Typically, a culture of the cell is incubated with a compound according to the invention at various concentrations for a period of time which is sufficient to enable the active agents to induce cell death or to inhibit cell proliferation, cell vitality or migration, usually between about one hour and one week. For testing in vitro, cultivated cells from a biopsy sample can be used. The amount of cells remaining after the treatment is then determined. The use in vitro takes place, in particular, on samples of mammal species which are suffering from cancer, tumours, metastases, angiogenesis disorders, retroviral diseases, immune diseases and/or pathogenic ageing processes. The host or patient can belong to any mammal species, for example a primate species, in particular humans, but also rodents (including mice, rats and hamsters), rabbits, horses, cows, dogs, cats, etc. Animal models are of interest for experimental investigations, providing a model for the treatment of a human disease.

The testing of a plurality of specific compounds enables the selection of the active compound which appears the most suitable for the treatment of the patient. The in-vivo dose of the selected compound is advantageously matched to the susceptibility of the kinase and/or severity of the disease of the patient taking into account the in-vitro data, as a result of which the therapeutic efficacy is noticeably increased. The dose varies depending on the specific compound used, the specific disease, the patient status, etc. A therapeutic dose is typically sufficient considerably to reduce the undesired cell population in the target tissue, while the viability of the patient is maintained. The following teaching of the invention and embodiments thereof relating to the use of compounds of the formula (I) for the preparation of a medicament for the prophylaxis, therapy and/or progress control is valid and can be applied without restrictions to the use of the compounds for the inhibition of the kinase activity, if it appears appropriate.

The treatment is generally continued until a considerable reduction has occurred, for example at least about 50% reduction of the cell load, and can be continued until essentially no more undesired cells are detected in the body. In tests of this type, the compounds according to the invention exhibit and cause an inhibiting effect, which is usually documented by $IC_{50}$ values in a suitable range, preferably in the micromolar range and more preferably in the nanomolar range. The kinase is inhibited, in particular, to the extent of 50% if the concentration of the compounds is less than 1 µM, preferably equal to or less than 0.5 µM, particularly preferably less than 0.1 µM. This concentration is called the $IC_{50}$ value.

The invention also relates to a medicament comprising at least one compound of the formula (I) or part-formulae thereof and/or physiologically acceptable salts, tautomers and/or stereoisomers thereof, including mixtures thereof in all ratios. The invention also relates to a pharmaceutical composition comprising, as active compound, an effective amount of at least one compound of the formula (I) or part-formulae thereof and/or physiologically acceptable salts, tautomers and/or stereoisomers thereof, including mixtures thereof in all ratios, together with pharmaceutically tolerated assistants.

A "medicament", "drug" and a "pharmaceutical composition" or "pharmaceutical formulation" here is any composition which can be employed in the prophylaxis, therapy, progress control or aftertreatment of patients who, at least temporarily, exhibit a pathogenic modification of the overall condition or the condition of individual parts of the patient organism, preferably as a consequence of cancer, tumours, metastases, angiogenesis disorders, retroviral diseases, immune diseases and/or accelerated ageing processes, particularly preferably as a consequence of cancer, tumours, metastases and/or angiogenesis disorders.

In order to increase the protective or therapeutic action of the compounds according to the invention, pharmaceutically tolerated adjuvants can be added. For the purposes of the invention, any substance which facilitates, enhances or modifies an effect with the compounds in accordance with the invention is an "adjuvant". Known adjuvants are, for example, aluminium compounds, such as, for example, aluminium hydroxide or aluminium phosphate, saponins, such as, for example, QS 21, muramyl dipeptide or muramyl tripeptide, proteins, such as, for example, gamma-interferon or TNF, MF 59, phosphatdibylcholine, squalene or polyols. The co-application of egg albumin in complete Freund's adjuvant can likewise cause increased cell-mediated immunity and thus support the action of neutralising antibodies formed. Furthermore, DNA, which has an immunostimulatory property, or which encodes a protein with an adjuvant effect, such as, for example, a cytokine, can be applied in parallel or in a construct.

The introduction of the pharmaceutical composition into a cell or organism can be carried out in accordance with the invention in any manner which enables the kinases to be brought into contact with the compounds present in the composition, as a consequence of which a response is induced. The pharmaceutical composition of the present invention can be administered orally, transdermally, transmucosally, transurethrally, vaginally, rectally, pulmonarily, enterally and/or parenterally. The type of administration selected depends on the indication, the dose to be administered, individual-specific parameters, etc. In particular, the various types of administration facilitate site-specific therapy, which minimises side effects and reduces the active-compound dose. Very particularly preferred injections are intradermal, subcutaneous, intramuscular or intravenous injection. The administration can be carried out, for example, with the aid of so-called vaccination guns or by means of syringes. It is also possible to prepare the substance as an aerosol, which is inhaled by the organism, preferably a human patient.

The administration forms of the pharmaceutical composition are prepared corresponding to the desired type of administration in a suitable dosage and in a manner known per se using the conventional solid or liquid vehicles and/or diluents and the assistants usually employed. Thus, pharmaceutically acceptable excipients known to the person skilled in the art can basically form part of the pharmaceutical composition according to the invention, where the amount of excipient material which is combined with the active compound in order to prepare a single dose varies depending on the individual to be treated and the type of administration. These pharmaceutically tolerated additives include salts, buffers, fillers, stabilisers, complexing agents, antioxidants, solvents, binders, lubricants, tablet coatings, flavours, dyes, preservatives, adjusters and the like. Examples of excipients of this type are water, vegetable oils, benzyl alcohols, alkylene glycol, polyethylene glycol, glycerol triacetate, gelatine, carbohydrates, such as, for example, lactose or starch, magnesium stearate, talc and Vaseline.

The pharmaceutical formulation can be in the form of a tablet, film tablet, dragee, lozenge, capsule, pill, powder, granules, syrup, juice, drops, solution, dispersion, suspension, suppository, emulsion, implant, cream, gel, ointment, paste, lotion, serum, oil, spray, aerosol, adhesive, plaster or bandage. Oral administration forms which are prepared are preferably tablets, film tablets, dragees, lozenges, capsules, pills, powders, granules, syrups, juices, drops, solutions, dispersions or suspensions—including as depot form. Furthermore, parenteral medicament forms, such as, for example, suppositories, suspensions, emulsions, implants or solutions, should be considered, preferably oily or aqueous solutions. For topical application, the medicament active compound is formulated in a conventional manner with at least one pharmaceutically acceptable vehicle, such as, for example, microcrystalline cellulose, and optionally further assistants, such as, for example, moisturisers, to give solid formulations which can be applied to the skin, such as, for example, creams, gels, ointments, pastes, powders or emulsions, or to give liquid formulations which can be applied to the skin, such as, for example, solutions, suspensions, lotions, sera, oils, sprays or aerosols. The pharmaceutical composition is preferably in the form of an injection solution. For the preparation of the injection solution, aqueous media, such as, for example, distilled water or physiological salt solutions, can be used, where the latter include acidic and basic addition salts. The pharmaceutical composition may also be in the form of a solid composition, for example in the lyophilised state, and can then be prepared before use by addition of a dissolving agent, such as, for example, distilled water. The person skilled in the art is familiar with the basic principles of the preparation of lyophilisates.

The concentration of the active compound in the formulation can be 0.1 to 100 per cent by weight. It is crucial that the pharmaceutical composition comprises, as active compound, an effective amount of the compound together with the pharmaceutically tolerated assistants. The terms "effective amount" or "effective dose" are used interchangeably herein and denote an amount of the pharmaceutical active compound which has a prophylactically or therapeutically relevant action on a disease or pathological change in cell, tissue, organ or mammal. A "prophylactic action" prevents the outbreak of a disease or even infection with a pathogen after ingress of individual representatives in such a way that subsequent spread thereof is greatly reduced or they are even completely deactivated. A "prophylactic action" also includes an increase in normal physiological function. Prophylaxis is advisable, in particular, if an individual has predispositions for the onset of the above-mentioned diseases, such as, for example, a family history, a gene defect or a recently survived disease. A "therapeutically relevant action" frees in part or full from one, more than one or all disease symptoms or results in the partial or complete reversal of one, more than one or all physiological or biochemical parameters which are associated with or causally involved in the disease or pathological change into the normal state. Progress control is also taken to be a type of therapeutic treatment if the compounds are administered at certain time intervals, for example in order completely to eliminate the symptoms of a disease. The respective dose or dose range for the administration of the compounds according to the invention is sufficiently large to achieve the desired prophylactic or therapeutic effect of induction of a biological or medical response. In general, the dose will vary with the age, constitution and gender of the patient, and the severity of the disease will be taken into account. It goes without saying that the specific dose, frequency and duration of administration are, in addition, dependent on a multiplicity of factors, such as, for example, the targeting and binding ability of the compounds, feeding habits of the individual to be treated, type of administration, excretion rate and combination with other drugs. The individual dose can be adjusted both with respect to the primary disease and also with respect to the occurrence of any complications. The precise dose can be established by a person skilled in the art using known means and methods. This teaching of the invention is valid and can be applied without restrictions to the pharmaceutical composition comprising the compounds of the formula (I), if it appears appropriate.

In an embodiment of the invention, the compounds are administered in a dose of 0.01 mg to 1 g per dosage unit, preferably between 1 to 700 mg, particularly preferably 5 to 100 mg. The daily dose is in particular between 0.02 and 100 mg/kg of body weight.

In order to support the medical effect, the pharmaceutical composition may, in an embodiment of the invention, also comprise one or more further active compounds, where simultaneous or successive administration is conceivable. The therapeutic effect of the pharmaceutical composition according to the invention can consist, for example, in certain anticancer agents having a better action through the inhibition of DNA-PK as a desired side effect or in the number of side effects of these medicaments being reduced by the reduction in the dose.

In a preferred embodiment of the invention, the pharmaceutical composition according to the invention is combined with an anticancer agent. As used here, the term "anticancer agent" relates to any agent which is administered to a patient with cancer, tumours, metastases and/or angiogenesis disorders for the purpose of treatment of the cancer. The anticancer agent is particularly preferably selected from the group comprising cytokines, chemokines, pro-apoptotic agents, interferons, radioactive compounds, oestrogen receptor modulators, androgen receptor modulators, retinoid receptor modulators, cytotoxic agents, cytostatic agents, prenyl-protein transferase inhibitors and angiogenesis inhibitors or combinations thereof. It is preferred for the anticancer agent to modify, in particular reduce, nucleic acid and/or protein metabolism, cell division, DNA replication, purine, pyrimidine and/or amino acid biosynthesis, gene expression, mRNA processing, protein synthesis, apoptosis or combinations thereof.

The invention can also be practised as a kit which comprises the compounds according to the invention. The kit consists of separate packs of (a) an effective amount of a compound of the formula (I) and/or physiologically acceptable salts, tautomers and/or stereoisomers thereof, including mixtures thereof in all ratios, and (b) an effective amount of a further active compound. The kit comprises suitable containers, such as, for example, boxes or cartons, individual bottles, bags or ampoules. The kit may, for example, comprise separate ampoules, each containing an effective amount of a compound of the formula (I) and/or pharmaceutically usable salts, tautomers and/or stereoisomers thereof, including mixtures thereof in all ratios, and an effective amount of a further medicament active compound in dissolved or lyophilised form. The kit of the invention may also contain an article which contains written instructions or points the user towards written instructions which explain the handling of the compounds of the invention.

In accordance with the invention, the compounds of the formula (I) or part-formulae thereof and/or physiologically acceptable salts, tautomers and/or stereoisomers thereof, including mixtures thereof in all ratios, are used for the prophylaxis, therapy and/or progress control of diseases which are caused, promoted and/or spread by the activity of serine/threonine protein kinases. The present invention therefore also relates to the use of compounds of the formula (I) or part-formulae thereof and/or physiologically acceptable salts, tautomers and/or stereoisomers thereof, including mixtures thereof in all ratios, for the preparation of a medicament for the prophylaxis, therapy and/or progress control of diseases which are caused, promoted and/or spread by the activity of serine/threonine protein kinases. In accordance with the invention, compounds of the formula (I) or part-formulae thereof and/or physiologically acceptable salts, tautomers and/or stereoisomers thereof, including mixtures thereof in all ratios, are suitable for use in the prophylaxis, therapy and/or progress control of diseases which are caused, promoted and/or spread by activity of serine/threonine protein kinases. For the identification of a corresponding signalling pathway and in order to detect interactions between various signalling pathways, suitable models or model systems have been developed, for example cell culture models (Khwaja et al. (1997) EMBO 16: 2783) and models of transgenic animals (White et al. (2001) Oncogene 20: 7064). In order to determine certain stages in the signalling cascade, interacting compounds can be used in order to modulate the signal (Stephens et al. (2000) Biochemical J 351: 95). In addition, the compounds according to the invention can also be used as reagents for testing kinase-dependent signalling pathways in animals and/or cell culture models or in the clinical diseases mentioned in this application. As discussed herein, these signalling pathways are relevant for various diseases. Accordingly, the compounds according to the invention are useful in the prophylaxis, therapy and/or progress control of diseases which are dependent on signalling pathways with participation by serine/threonine protein kinases.

In accordance with the invention, the compounds of the formula (I) or part-formulae thereof and/or physiologically acceptable salts, tautomers and/or stereoisomers thereof, including mixtures thereof in all ratios, are suitable for use in the prophylaxis, therapy and/or progress control of cancer, tumours, metastases, angiogenesis disorders, retroviral diseases and/or immune diseases, in particular cancer, tumours, metastases and/or angiogenesis disorders. In accordance with the invention, the compounds of the formula (I) or part-formulae thereof and/or physiologically acceptable salts, tautomers and/or stereoisomers thereof, including mixtures thereof in all ratios, are also suitable for use in the slowing of ageing processes, where the slowing takes place with reference to the comparison of the life span of the treated host or cells, cell cultures, tissues or organs thereof with corresponding positive or negative controls and/or statistics. It goes without saying that the host of the pharmaceutical compounds is also included in the scope of protection of the present invention.

The tumour is, in particular, selected from the group of diseases of squamous epithelium, bladder, stomach, kidneys, head, neck, oesophagus, cervix, thyroid, intestine, liver, brain, prostate, urogenital tract, lymphatic system, larynx, lung, skin, blood and immune system, and/or the cancer is selected from the group of monocytic leukaemia, lung adenocarcinoma, small-cell lung carcinoma, pancreatic cancer, glioblastoma, bowel carcinoma, breast carcinoma, acute myeloid leukaemia, chronic myeloid leukaemia, acute lymphatic leukaemia, chronic lymphatic leukaemia, Hodgkin's lymphoma and non-Hodgkin's lymphoma.

A further embodiment of the present invention relates to the compounds according to the invention in combination with radiotherapy and/or with at least one further active compound, preferably in combination with radiotherapy and/or an anticancer agent. Industrial irradiation methods which are used clinically preferably include photon irradiation (classical, electromagnetic X-ray/gamma radiation), proton irradiation, heavy-ion irradiation (ionised carbon) and neutron irradiation, without being restricted thereto. These radiotherapies and other suitable irradiation therapies in the sense of the invention are known to the person skilled in the art, such as, for example, from Herrmann et al. (2006) Klinische Strahlen-biologie [Clinical Radiation Biology], Elsevier Munich, 4th Edition, 67-68; Bhide & Nutting (2010) BMC Medicine 8: 25; Choi & Hung (2010) Current Urology Reports 11(3): 172. As the most frequent application, photon irradiation has been refined technically by the IMRT (intensity-modulated radiotherapy) method and by imaging methods (three-dimensional conformal radiotherapy) in irradiation planning and performance for the most precise focusing possible. The compounds according to the invention achieve synergistic effects in existing cancer chemotherapies and irradiations and/or restore the efficacy of existing cancer chemotherapies and irradiations. The synergistic action of the inhibition of VEGF in combination with radiotherapy is described in the prior art (WO 00/61186). The further medicament active compounds are particularly preferably chemotherapeutic agents which inhibit angiogenesis and thus inhibit the growth and spread of tumour cells. Examples thereof are VEGF receptor inhibitors, comprising ribozymes and antisense which are directed at VEGF receptors, and angiostatin and endostatin. Further examples of antineoplastic agents which can be used in combination with the compounds according to the invention generally include alkylating agents, antimetabolites, epidophyllotoxin, an antineoplastic enzyme, a topoisomerase inhibitor, procarbazine, mitoxantrone or platinum coordination complexes. In another embodiment, the anticancer agent is particularly preferably selected from the group of oestrogen receptor modulator, androgen receptor modulator, retinoid receptor modulator, cytotoxic agent, cytostatic agent, prenyl-protein transferase inhibitor and angiogenesis inhibitor. In addition, the previous teaching of the invention and embodiments thereof relating to pharmaceutical composition is valid and can be applied without restrictions to the second medical indication, if it appears appropriate. A very particularly preferred embodiment encompasses the compounds according to the invention in combination with radiotherapy and/or a cytostatic agent.

Still a further embodiment of the invention relates to the use of at least one compound of the formula (I) and/or physiologically acceptable salts, tautomers and/or stereoisomers thereof, including mixtures thereof in all ratios, for the sensitisation of cancer cells to an anticancer agent and/or ionising radiation, with the proviso that the sensitisation does not take place in vivo on the human or animal body. The sensitisation preferably takes place ex vivo or in vitro by administering the compounds to cells, cell cultures, tissues or organs which comprise serine/threonine protein kinases. The ex-vivo use is used, in particular, in the case of animal cells which originate from an animal organism which is affected by a disease which is selected from the group of cancer, tumours, metastases and/or angiogenesis disorders. The cells treated ex vivo can either continue to be kept in culture for subsequent investigations or transferred into an animal, which can be the host animal or another animal. The ex-vivo sensitisation according to the invention is particularly advantageous for testing the specific action of the compounds, so that the in-vivo dose can be pre-adjusted correspondingly with evaluation of these ex-vivo data. As a result thereof, the therapeutic effect is increased significantly. Alternatively, the invention is also designed for use in-vivo and relates to at least one compound of the formula (I) and/or physiologically acceptable salts, tautomers and/or stereoisomers thereof, including mixtures thereof in all ratios, for use for the sensitisation of cancer cells to an anticancer agent and/or ionising radiation.

The invention furthermore teaches a method for the prophylaxis, therapy and/or progress control of cancer, tumours, metastases, angiogenesis disorders, retroviral diseases, immune diseases and/or ageing processes in which an effective amount of at least one compound according to the invention and/or physiologically acceptable salts, tautomers and/or stereoisomers thereof, including mixtures thereof in all ratios, is administered to a subject to be treated. Preferred subjects in the sense of the invention are humans or animals, particularly preferably humans. It is known to the person skilled in the art here that he can administer the compounds according to the invention, which can of course also be used as the pharmaceutical composition according to the invention, in various doses to an organism, in particular a human patient. The effective amount and the type of administration can be determined by the person skilled in the art by routine experiments. The previous teaching of the invention and embodiments thereof are valid and can be applied without restrictions to the treatment method, if it appears appropriate.

All said and further constituents or components are familiar to the person skilled in the art and can experience a specific embodiment for the teaching according to the invention in routine experiments. All documents cited in the description are hereby intended to be incorporated in their entirety into the disclosure of the present invention as reference.

As part of the invention presented here, novel 2,3-dihydro-1H-imidazol[4,5-c]quinoline compounds of the formula (I) were provided for the first time. The compounds according to the invention control serine/threonine protein kinases, in particular DNA-PK, affinitively and/or selectively. The compounds from formula (I) and derivatives thereof are distinguished by high specificity and stability, low preparation costs and easy handling. These properties form the basis for a reproducible mode of action, including the absence of cross-reactivities, and reliable and safe interaction with the corresponding target structures. The invention also includes the use of the present 2,3-dihydro-1H-imidazol[4,5-c]quinoline derivatives for the inhibition, regulation and/or modulation of the signalling cascade of serine/threonine protein kinases, in particular DNA-PK, and thus offers novel tools for research and/or diagnostics.

Medicaments and pharmaceutical compositions which comprise the said compounds and the use of these compounds for the treatment of kinase-promoted disorders are, in addition, a highly promising approach for a broad spectrum of therapies, enabling direct and immediate alleviation of symptoms to be achieved in humans and animals. This is particularly advantageous for effective combating of severe diseases, such as cancer, either as monotherapy or in combination with other antineoplastic therapies. The key participation by DNA-PK in DNA repair processes and the evidence that the DNA-PK inhibitors allows mammal cells to become more radiation-sensitive enable therapeutic use of DNA-PK or DNA-PK/ATM or ATM-specific inhibitors as part of the treatment of, for example, solid cancer tumours by radiotherapy and/or chemotherapy aimed at DNA-DSBs. The compounds of the formula (I), salts, isomers, tautomers, enantiomers, diastereomers, racemates, derivatives, prodrugs and/or metabolites thereof are effective not only in the case of the said clinical disease pictures, but likewise in the diagnosis and therapy of all diseases in connection with the DNA-PK signalling cascade, in particular with respect to the inhibition of cell proliferation and migration. In addition, the inhibitors according to the invention can be used in the treatment of retroviral diseases by suppression of retroviral integration (R. Daniel (1999) Science 284: 644). Finally, the inhibitors according to the invention can be employed as immunomodulators and modulators of telomeric maintenance. The low-molecular-weight inhibitors are used individually and/or in combination with other treatment measures, such as, for example, surgical interventions, immunotherapy, radiotherapy and/or chemotherapy. The latter relate to targeted therapy with any desired NME (i.e. NCE and/or NBE) as monotherapy and/or on-target/off-target combination therapy.

Owing to their surprisingly strong and/or selective inhibition of enzymes which regulate cellular processes via the repair of dsDNA, the compounds of the invention can be administered in advantageously low dose, while they achieve a similar or even superior biological efficacy compared with the less-potent or less-selective inhibitors of the prior art. The reduced dose is also accompanied by reduced or no medical side effects. In addition, the highly selective inhibition by the compounds according to the invention is also reflected by a reduction in undesired side effects, which is independent of the dose.

It goes without saying that this invention is not restricted to the specific compounds, pharmaceutical compositions, uses and methods as described herein, since such things can be varied. It furthermore goes without saying that the terminology used here serves exclusively the purpose of description of particular embodiments and is not intended to restrict the scope of protection of the invention. As used here in the specification, including the appended claims, word forms in the singular, such as, for example, "a" or "the", include the equivalent in the plural, so long as the context does not specifically indicate otherwise. For example, the reference to "a compound" includes a single compound or a plurality of compounds, which may in turn be identical or different, or the reference to "a method" includes equivalent steps and methods which are known to the person skilled in the art.

The invention is explained in greater detail below with reference to non-limiting examples of specific embodiments. The examples should, in particular, be interpreted as not being restricted to the feature combinations specifically illustrated, but instead the illustrative features can in turn be freely combined so long as the object of the invention is achieved.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, evaporated and purified by chromatography on silica gel and/or by crystallisation. Rf values on silica gel; eluent: ethyl acetate/methanol 9:1.

NMR (1H) was carried out with the following parameters.
Instruments: Bruker Avance DRX 500, Bruker Avance 400, Bruker DPX 300
Reference: TMS
TD (time domain=number of data points or digital resolution): 65536
Solvent: DMSO d6
NS (number of scans): 32
SF (spectrometer frequency=transmission frequency): 500 MHz
TE (temperature): 303 K
HPLC-MS was carried out with the following parameters.
Instrument: Agilent Technologies 1200 series
Methods: ESI1 ROD.M and POLAR.M (3.8 min., solvent gradient)
Column: ChromolithSpeedROD RP18e50-4.6
Solvent: acetonitrile+0.05% of HCOOH/deionised water+ 0.04% of HCOOH
Detection wavelength: 220 nm
MS type: API-ES

EXAMPLE 1
Synthesis of 3-fluoro-4-(8-hydroxy-7-methoxy-3-methyl-2-oxo-2,3-dihydroimidazo[4,5-c]quinolin-1-yl)benzonitrile
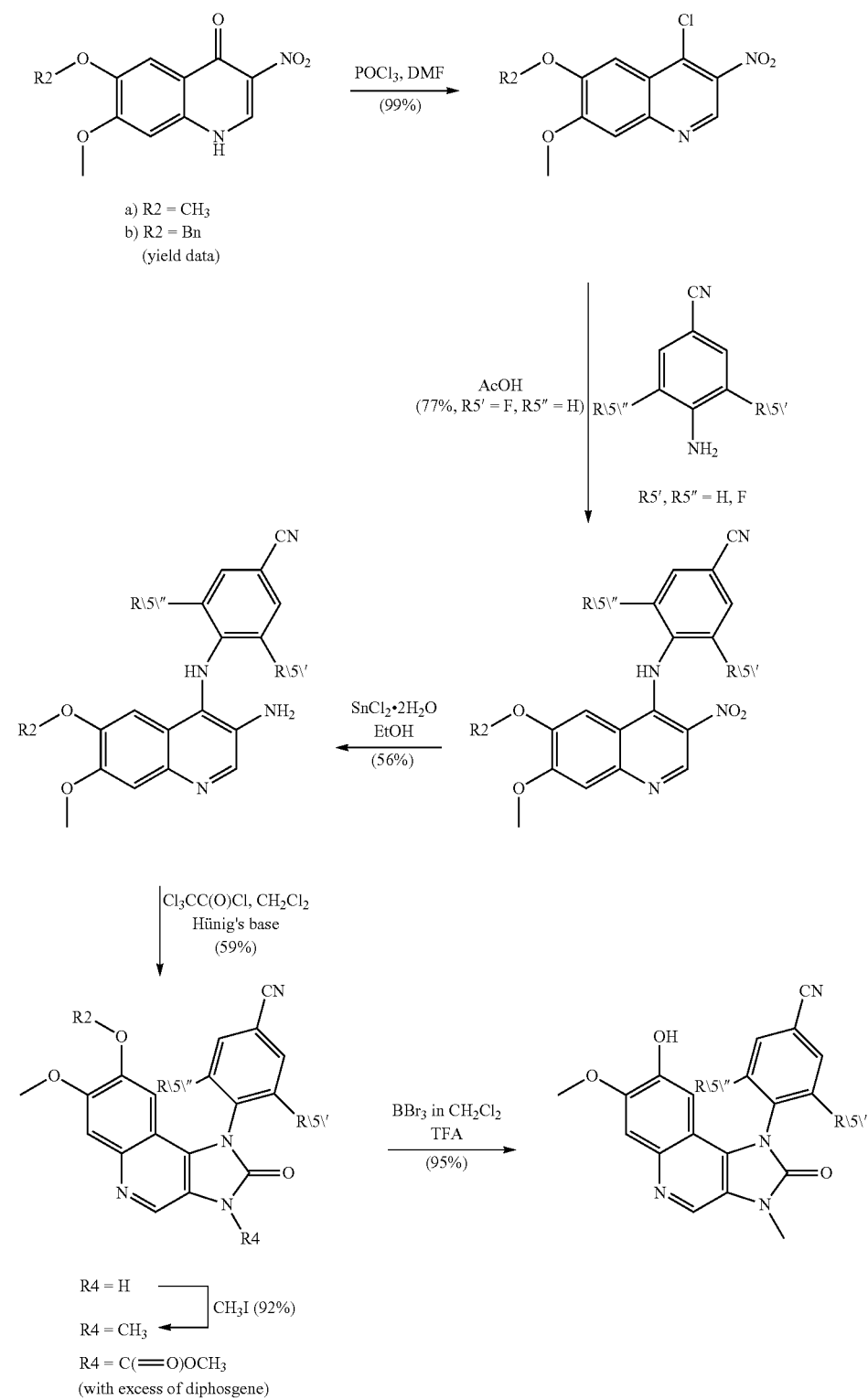

6-Benzyloxy-7-methoxy-3-nitro-1H-quinolin-4-one (9.10 g, 27.89 mmol, see Acta Pharmacologica Sinica 2008, 29(12), 1529-1538) was suspended in dry N,N-dimethylformamide (70 ml). Phosphoryl chloride (2.82 ml, 30.68 mmol) was subsequently added, and the mixture was heated at 100° C. for 30 min. After cooling, the reaction mixture was added to ice-water (500 ml) with stirring and stirred for a further 30 min. The precipitate formed was filtered off with suction, washed with water and dried in vacuo, giving 6-benzyloxy-4-chloro-7-methoxy-3-nitroquinoline (9.57 g, 27.76 mmol) as solid. MS: 345.1 (M+H$^+$), TLC (HPTLC): R$_f$=0.44 (cyclohexane/ethyl acetate 2:1, parts by volume).

6-Benzyloxy-4-chloro-7-methoxy-3-nitroquinoline (6.75 g, 19.58 mmol) and 4-amino-3-fluorobenzonitrile (2.46 g, 18.1 mmol) were dissolved in glacial acetic acid (106 ml) and stirred at 50° C. for 18 h overnight. The suspension obtained was subsequently added to water (1l) and stirred for a further 30 min. The precipitate formed was filtered off with suction, rinsed with water and dried in vacuo, giving 4-(6-benzyloxy-7-methoxy-3-nitro-quinolin-4-ylamino)-3-fluorobenzonitrile (6.69 g, 15.06 mmol) as solid. MS: 445.1 (M+H$^+$), TLC (HPTLC): R$_f$=0.31 (cyclohexane/ethyl acetate 2:1, parts by volume).

4-(6-Benzyloxy-7-methoxy-3-nitroquinolin-4-ylamino)-3-fluorobenzonitrile (6.50 g, 14.62 mmol) and tin(II) chloride dihydrate (14.70 g, 65.15 mmol) were dissolved in ethanol (780 ml). The reaction solution was subsequently stirred at 70° C. for 30 min. When the reaction was complete (TLC, LC-MS), water (2 l) and ethyl acetate (1.5 l) was added, and the mixture was stirred vigorously for a further 30 min. The suspension obtained was filtered through kieselguhr. The aqueous phase was extracted again with ethyl acetate (1 l), and the combined organic phases were washed with water (500 ml). After the organic phase had been dried over Na$_2$SO$_4$, the solid material was filtered off with suction, and the filtrate was evaporated to dryness in vacuo, giving 4-(3-amino-6-benzyloxy-7-methoxyquinolin-4-ylamino)-3-fluorobenzonitrile (3.40 g, 8.2 mmol) as solid. MS: 415.1 (M+H$^+$), TLC (HPTLC): R$_f$=0.47 (ethyl acetate).

4-(3-Amino-6-benzyloxy-7-methoxyquinolin-4-ylamino)-3-fluorobenzonitrile (2.99 g, 7.2 mmol) was dissolved in dichloromethane (69 ml) together with Hünig's base (iPr$_2$EtN, 1.43 ml). The solution obtained was subsequently added dropwise with ice-bath cooling to a mixture of trichloromethyl chloroformate (diphosgene, 938 µl, 7.72 mmol) and dichloromethane (42 ml). When the addition was complete, the mixture was stirred at room temperature for a further 30 min. Saturated Na$_2$CO$_3$ (30 ml) and water (170 ml) were subsequently added. After stirring for a further 30 min, the mixture was extracted twice with ethyl acetate (225 ml each time). The combined organic phases were washed once with water (150 ml), dried over Na$_2$SO$_4$, filtered and evaporated to dryness in vacuo. The residue was chromatographed over flash silica gel (solvent gradient ethyl acetate/0-17% by vol. of ethanol), giving 4-(8-benzyloxy-7-methoxy-2-oxo-2,3-dihydroimidazo[4,5-c]quinolin-1-yl)-3-fluorobenzonitrile (1.87 g, 4.3 mmol) as solid. MS: 441.1 (M+H$^+$), TLC (HPTLC): R$_f$=0.44 (ethyl acetate/ethanol 8:1, parts by volume).

Benzyloxy-7-methoxy-2-oxo-2,3-dihydroimidazo[4,5-c]quinolin-1-yl)-3-fluorobenzonitrile (1.73 g, 3.93 mmol) was dissolved in N,N-dimethylformamide (40 ml). Iodomethane (294 µl, 4.7 mmol) and K$_2$CO$_3$ (1.09 g, 7.86 mmol) were subsequently added. The reaction mixture was stirred at room temperature for 18 h overnight. The suspension was then added to water (600 ml) and stirred for a further 30 min. The precipitate was filtered off, rinsed with water and chromatographed over flash silica gel (solvent gradient dichloromethane/0-15% by vol. of methanol), giving 4-(8-benzyloxy-7-methoxy-3-methyl-2-oxo-2,3-dihydroimidazo[4,5-c]quinolin-1-yl)-3-fluorobenzonitrile (1.64 g, 3.61 mmol) as solid. MS: 455.1 (M+H$^+$), TLC (HPTLC): R$_f$=0.34 (ethyl acetate/ethanol 8:1, parts by volume).

$^1$H NMR (400 MHz, DMSO) δ=8.78 (s, 1H), 8.23-8.16 (m, 1H), 8.00-7.86 (m, 2H), 7.46 (s, 1H), 7.40-7.29 (m, 3H), 7.18-7.10 (m, 2H), 6.27 (s, 1H), 4.85-4.73 (m, 2H), 3.92 (s, 3H), 3.54 (s, 3H).

A boron tribromide solution in dichloromethane (1.0 M, 14.5 ml, 14.5 mmol) was slowly added dropwise with ice-bath cooling in a dry nitrogen atmosphere to a solution of 4-(8-benzyloxy-7-methoxy-3-methyl-2-oxo-2,3-dihydroimidazo[4,5-c]quinolin-1-yl)-3-fluorobenzonitrile (1.45 g, 3.19 mmol) in trifluoroacetic acid (29 ml). When the addition was complete, the mixture were subsequently stirred for a further 30 min. When the reaction was complete (HPLC-MS check), the reaction mixture was carefully added to water (700 ml) and extracted twice with ethyl acetate (290 ml each time). The combined organic phases were washed with water (100 ml) and semi-saturated NaHCO$_3$ solution (150 ml), subsequently dried using Na$_2$SO$_4$ and filtered with suction. The filtrate was evaporated in vacuo, and the residue was chromatographed over flash silica gel (solvent gradient ethyl acetate/0-33% by vol. of ethanol), giving 3-fluoro-4-(8-hydroxy-7-methoxy-3-methyl-2-oxo-2,3-dihydroimidazo[4,5-c]quinolin-1-yl)benzonitrile (1.10 g, 3.03 mmol), as solid. MS: 365.1 (M+H$^+$), TLC (HPTLC): R$_f$=0.46 (ethyl acetate/ethanol 2:1, parts by volume).

$^1$H NMR (400 MHz, DMSO) δ=9.93 (s, 1H), 8.73 (s, 1H), 8.32 (dd, J=9.7, 1.5, 1H), 8.09-7.93 (m, 2H), 7.39 (s, 1H), 6.32 (s, 1H), 3.89 (s, 3H), 3.54 (s, 3H).

Compounds which were prepared in accordance with Example 1 are shown in Table 2 below.

TABLE 2

Compounds of the formulae (I) and (IA)

| No. | Structural formula | Name | Analysis | IC$_{50}$ DNA-PK [μM] |
|---|---|---|---|---|
| 1 | | 4-(7,8-Dimethoxy-2-oxo-2,3-dihydroimidazo[4,5-c]quinolin-1-yl)benzonitrile | MS: 347.1 (M + H$^+$), TLC (HPTLC): R$_f$ = 0.48 (ethyl acetate/ethanol 8:1, parts by volume) | <0.1 |
| 2 | | 4-(7,8-Dimethoxy-3-methyl-2-oxo-2,3-dihydroimidazo-[4,5-c]quinolin-1-yl)-benzonitrile | MS: 361.1 (M + H$^+$), TLC (HPTLC): R$_f$ = 0.46 (ethyl acetate/ethanol 8:1, parts by volume) | <0.1 |
| 3 | | 4-(8-Hydroxy-7-methoxy-3-methyl-2-oxo-2,3-dihydro-imidazo[4,5-c]quinolin-1-yl)-benzonitrile | MS: 347.1 (M + H$^+$), TLC (HPTLC): R$_f$ = 0.32 (ethyl acetate/ethanol 2:1, parts by volume) | <0.1 |
| 4 | | 3-Fluoro-4-(8-hydroxy-7-methoxy-3-methyl-2-oxo-2,3-dihydroimidazo[4,5-c]quinolin-1-yl)benzonitrile | MS: 365.1 (M + H$^+$), TLC (HPTLC): R$_f$ = 0.46 (ethyl acetate/ethanol 2:1, parts by volume) | <0.1 |

TABLE 2-continued

Compounds of the formulae (I) and (IA)

| No. | Structural formula | Name | Analysis | IC$_{50}$ DNA-PK [μM] |
|---|---|---|---|---|
| 5 | | 3,5-Difluoro-4-(8-hydroxy-7-methoxy-3-methyl-2-oxo-2,3-dihydroimidazo[4,5-c]quinolin-1-yl)benzonitrile | MS: 383.1 (M + H$^+$), TLC (HPTLC): R$_f$ = 0.35 (ethyl acetate/ethanol 5:1, parts by volume) | >0.1 |
| 6 | | 4-(8-Benzyloxy-7-methoxy-2-oxo-2,3-dihydroimidazo-[4,5-c]quinolin-1-yl)-benzonitrile | MS: 423.1 (M + H$^+$), TLC (HPTLC): R$_f$ = 0.51 (ethyl acetate/ethanol 8:1, parts by volume) | <0.1 |
| 7 | | 4-(8-Benzyloxy-7-methoxy-3-methyl-2-oxo-2,3-dihydro-imidazo[4,5-c]quinolin-1-yl)-benzonitrile | MS: 437.1 (M + H$^+$), TLC (HPTLC): R$_f$ = 0.44 (ethyl acetate/ethanol 8:1, parts by volume) | <0.1 |
| 8 | | 4-(8-Benzyloxy-7-methoxy-2-oxo-2,3-dihydroimidazo-[4,5-c]quinolin-1-yl)-3-fluorobenzonitrile | MS: 441.1 (M + H$^+$), TLC (HPTLC): R$_f$ = 0.52 (ethyl acetate/ethanol 5:1, parts by volume) | <0.1 |

TABLE 2-continued

Compounds of the formulae (I) and (IA)

| No. | Structural formula | Name | Analysis | IC$_{50}$ DNA-PK [µM] |
|---|---|---|---|---|
| 9 | | 4-(8-Benzyloxy-7-methoxy-3-methyl-2-oxo-2,3-dihydro-imidazo[4,-c]quinolin-1-yl)-3-fluorobenzonitrile | MS: 455.1 (M + H$^+$), TLC (HPTLC): R$_f$ = 0.42 (ethyl acetate/ethanol 5:1, parts by volume) | <0.1 |
| 10 | | 4-(8-Benzyloxy-7-methoxy-2-oxo-2,3-dihydroimidazo-[4,5-c]quinolin-1-yl)-3,5-difluorobenzonitrile | MS: 459.1 (M + H$^+$), TLC (HPTLC): R$_f$ = 0.42 (ethyl acetate/ethanol 5:1, parts by volume) | <0.1 |
| 11 | | 4-(8-Benzyloxy-7-methoxy-3-methyl-2-oxo-2,3-dihydro-imidazo[4,5-c]quinolin-1-yl)-3,5-difluorobenzonitrile | MS: 473.1 (M + H$^+$), TLC (HPTLC): R$_f$ = 0.41 (ethyl acetate/ethanol 5:1, parts by volume) | <0.1 |

TABLE 2-continued

Compounds of the formulae (I) and (IA)

| No. | Structural formula | Name | Analysis | IC$_{50}$ DNA-PK [µM] |
|---|---|---|---|---|
| 12 | 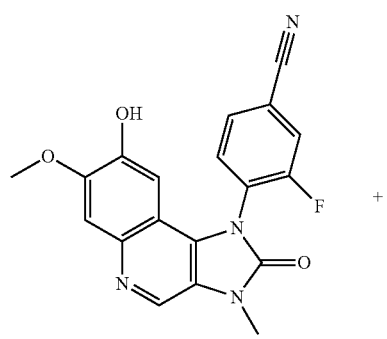 | Methyl 8-benzyloxy-1-(4-cyano-2-fluorophenyl)-7-methoxy-2-oxo-1,2-dihydroimidazo[4,5-c]-quinoline-3-carboxylate | MS: 499.2 (M + H$^+$), TLC (HPTLC): R$_f$ = 0.70 (ethyl acetate/ethanol 5:1, parts by volume) | <0.1 |

EXAMPLE 2

Synthesis of 3-fluoro-4-(7-methoxy-3-methyl-2-oxo-8-(thiophen-3-ylmethoxy)-2,3-dihydroimidazo[4,5-c]quinolin-1-yl)benzonitrile

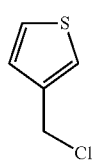

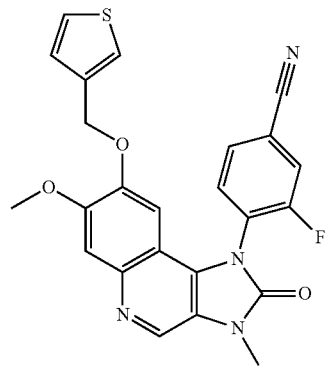

3-Fluoro-4-(8-hydroxy-7-methoxy-3-methyl-2-oxo-2,3-dihydroimidazo[4,5-c]quinolin-1-yl)-benzonitrile (80 mg, 220 µmol) was dissolved in N,N-dimethylformamide (4.0 ml) under a dry argon atmosphere. Potassium carbonate (85 mg, 618 µmol) and 3-chloromethylthiophene (112 mg, 845 µmol; prepared from 3-thiophenemethanol using SOCl$_2$ in CH$_2$Cl$_2$) were subsequently added. The reaction mixture was stirred at 50° C. for 18 h overnight. When the reaction was complete, the mixture was poured into water (60 ml), stirred for 30 min and extracted twice with ethyl acetate (75 ml each time). The combined organic phases were washed with water (25 ml), subsequently dried over Na$_2$SO$_4$, filtered with suction and evaporated in vacuo. The residue chromatographed over flash silica gel (solvent gradient ethyl acetate/0-17% by vol. of ethanol), giving 3-fluoro-4-(7-methoxy-3-methyl-2-oxo-8-(thiophen-3-ylmethoxy)-2,3-dihydroimidazo[4,5-c]quinolin-1-yl)benzonitrile (64 mg, 139 µmol), as solid. MS: 461.1 (M+H$^+$), TLC (HPTLC): R$_f$=0.33 (ethyl acetate/ethanol 5:1, parts by volume).

Compounds which were prepared in accordance with the synthetic procedure from Example 2 are shown in Table 3 below.

TABLE 3

Compounds of the formulae (I) and (IA)

| No. | Structural formula | Name | Analysis | IC$_{50}$ DNA-PK [μM] |
|---|---|---|---|---|
| 13 | | 3-Fluoro-4-(7-methoxy-3-methyl-2-oxo-8-(thiophen-3-ylmethoxy)-2,3-dihydroimidazo[4,5-c]-quinolin-1-yl)benzonitrile | MS: 461.1 (M + H$^+$), TLC (HPTLC): R$_f$ = 0.33 (ethyl acetate/ethanol 5:1, parts by volume) | <0.1 |
| 14 | | 3-Fluoro-4-(7-methoxy-3-methyl-2-oxo-8-(thiophen-2-ylmethoxy)-2,3-dihydroimidazo[4,5-c]-quinolin-1-yl)benzonitrile | MS: 461.1 (M + H$^+$), TLC (HPTLC): R$_f$ = 0.61 (ethyl acetate/ethanol 2:1, parts by volume) | <0.1 |
| 15 | | 2-[1-(4-Cyano-2-fluorophenyl)-7-methoxy-3-methyl-2-oxo-2,3-dihydro-1H-imidazo[4,5-c]-quinolin-8-yloxy]-2-(4-fluoro-phenyl)acetamide | MS: 516.1 (M + H$^+$), TLC (HPTLC): R$_f$ = 0.41-0.50 (ethyl acetate/ethanol 2:1, parts by volume) | <0.1 |

TABLE 3-continued

Compounds of the formulae (I) and (IA)

| No. | Structural formula | Name | Analysis | IC$_{50}$ DNA-PK [μM] |
|---|---|---|---|---|
| 16 | | 2-[1-(4-Cyano-2-fluorophenyl)-7-methoxy-3-methyl-2-oxo-2,3-dihydro-1H-imidazo[4,5-c]-quinolin-8-yloxy]-2-(4-fluoro-phenyl)-N-(2-methoxyethyl)-acetamide | MS: 574.2 (M + H$^+$), TLC (HPTLC): R$_f$ = 0.29-0.37 (ethyl acetate/ethanol 2:1, parts by volume) | 0.1-0.5 |
| 17 | | 3-Fluoro-4-[8-(4-fluoro-benzyloxy)-7-methoxy-3-methyl-2-oxo-2,3-dihydro-imidazo[4,5-c]quinolin-1-yl]-benzonitrile | MS: 473.1 (M + H$^+$), TLC (HPTLC): R$_f$ = 0.47 (ethyl acetate/ethanol 2:1, parts by volume) | <0.1 |
| 18 | | 2-[1-(4-Cyano-2-fluorophenyl)-7-methoxy-3-methyl-2-oxo-2,3-dihydro-1H-imidazo[4,5-c]-quinolin-8-yloxy]-2-phenyl-acetamide | MS: 498.1 (M + H$^+$), TLC (HPTLC): R$_f$ = 0.27-0.38 (ethyl acetate/ethanol 5:1, parts by volume) | <0.1 |

TABLE 3-continued

Compounds of the formulae (I) and (IA)

| No. | Structural formula | Name | Analysis | IC$_{50}$ DNA-PK [μM] |
|---|---|---|---|---|
| 19 | | 3-Fluoro-4-{7-methoxy-3-methyl-8-[3-(morpholine-4-sulfonyl)-thiophen-2-ylmethoxy]-2-oxo-2,3-dihydro-1H-imdiazo[4,5-c]-quinolin-1-yl}benzonitrile | MS: 610.1 (M + H$^+$), TLC (HPTLC): R$_f$ = 0.53 (ethyl acetate/ethanol 2:1, parts by volume) | 0.1-0.5 |
| 20 | | 3-Fluoro-4-[7-methoxy-3-methyl-2-oxo-8-(pyridin-4-ylmethoxy)-2,3-dihydroimidazo[4,5-c]-quinolin-1-yl]benzonitrile | MS: 456.1 (M + H$^+$), TLC (HPTLC): R$_f$ = 0.36 (ethyl acetate/ethanol 2:1, parts by volume) | <0.1 |
| 21 | | 4-[8-(2-Bromobenzyloxy)-7-methoxy-3-methyl-2-oxo-2,3-dihydroimidazo[4,5-c]quinolin-1-yl]-3-fluorobenzonitrile | MS: 533.0/535.0 (M + H$^+$) (monobromo isotope distribution approx. 100:98), TLC (HPTLC): R$_f$ = 0.49 (ethyl acetate/ethanol 2:1, parts by volume) | <0.1 |

TABLE 3-continued

Compounds of the formulae (I) and (IA)

| No. | Structural formula | Name | Analysis | IC$_{50}$ DNA-PK [μM] |
|---|---|---|---|---|
| 22 | | 4-[8-(2-Bromo-4-fluorobenzyloxy)-7-methoxy-3-methyl-2-oxo-2,3-dihydro-imidazo[4,5-c]quinolin-1-yl]-3-fluorobenzonitrile | MS: 551.0/553.0 (M + H$^+$) (monobromo isotope distribution approx. 100:98), TLC (HPTLC): R$_f$ = 0.49 (ethyl acetate/ethanol 2:1, parts by volume) | <0.1 |
| 23 | | 4-[8-(2-Chloro-4-fluorobenzyloxy)-7-methoxy-3-methyl-2-oxo-2,3-dihydro-imidazo[4,5-c]quinolin-1-yl]-3-fluorobenzonitrile | MS: 507.0/509.0 (M + H$^+$), (monochloro isotope distribution approx. 100:32) TLC (HPTLC): R$_f$ = 0.51 (ethyl acetate/ethanol 2:1, parts by volume) | <0.1 |
| 24 | | 4-[8-(3-Chloro-4-fluorobenzyloxy)-7-methoxy-3-methyl-2-oxo-2,3-dihydro-imidazo[4,-c]quinolin-1-yl]-3-fluorobenzonitrile | MS: 507.0/509.0 (M + H$^+$), (monochloro isotope distribution approx. 100:32) TLC (HPTLC): R$_f$ = 0.53 (ethyl acetate/ethanol 5:1, parts by volume) | <0.1 |

TABLE 3-continued

Compounds of the formulae (I) and (IA)

| No. | Structural formula | Name | Analysis | IC$_{50}$ DNA-PK [μM] |
|---|---|---|---|---|
| 25 | | 2-[1-(4-Cyano-2,6-difluoro-phenyl)-7-methoxy-3-methyl-2-oxo-2,3-dihydro-1H-imidazo-[4,5-c]quinolin-8-yloxy]-2-(4-fluorophenyl)acetamide | MS: 534.1 (M + H$^+$), TLC (HPTLC): R$_f$ = 0.44 (ethyl acetate/ethanol 5:1, parts by volume) | <0.1 |
| 26 | | 3,5-Difluoro-4-(7-methoxy-3-methyl-2-oxo-8-(thiophen-3-ylmethoxy)-2,3-dihydroimidazo-[4,5-c]quinolin-1-yl)benzonitrile | MS: 479.1 (M + H$^+$), TLC (HPTLC): R$_f$ = 0.50 (ethyl acetate/ethanol 5:1, parts by volume) | <0.1 |
| 27 | | 3,5-Difluoro-4-[8-(4-fluoro-benzyloxy)-7-methoxy-3-methyl-2-oxo-2,3-dihydroimidazo-[4,5-c]quinolin-1-yl]benzonitrile | MS: 491.1 (M + H$^+$), TLC (HPTLC): R$_f$ = 0.50 (ethyl acetate/ethanol 5:1, parts by volume) | <0.1 |

TABLE 3-continued

Compounds of the formulae (I) and (IA)

| No. | Structural formula | Name | Analysis | IC$_{50}$ DNA-PK [µM] |
|---|---|---|---|---|
| 28 | | 3,5-Difluoro-4-(7-methoxy-3-methyl-2-oxo-8-(thiophen-2-ylmethoxy)-2,3-dihydroimidazo-[4,5-c]quinolin-1-yl)benzonitrile | MS: 479.1 (M + H$^+$), TLC (HPTLC): R$_f$ = 0.72 (ethyl acetate/ethanol 5:1, parts by volume) | <0.1 |
| 29 | | 4-(7-Methoxy-3-methyl-2-oxo-8-(thiophen-3-ylmethoxy)-2,3-dihydroimidazo[4,5-c]quinolin-1-yl)benzonitrile | MS: 443.1 (M + H$^+$), TLC (HPTLC): R$_f$ = 0.50 (ethyl acetate/ethanol 8:1, parts by volume) | <0.1 |

EXAMPLE 3a

Synthesis of 3-fluoro-4-[7-methoxy-3-methyl-2-oxo-8-(thiazol-5-ylmethoxy)-2,3-dihydroimidazo[4,5-c]quinolin-1-yl)benzonitrile For the preparation, see also synthesis of 2-trimethylsilanylethyl {2-[1-(4-cyano-2-fluorophenyl)-7-methoxy-3-methyl-2-oxo-2,3-dihydro-1H-imidazo[4,5-c]quinolin-8-yloxy]-2-thiophen-2-ylethyl}carbamate under Example 3b:

3-fluoro-4-(8-hydroxy-7-methoxy-3-methyl-2-oxo-2,3-dihydroimidazo[4,5-c]quinolin-1-yl)benzonitrile (63 mg, 173 µmol), triphenylphosphine (polymer-bound) (294 mg, 1.12 mmol), thiazol-5-ylmethanol (62 mg, 540 µmol), diisopropyl azodicarboxylate (166 µl, 845 µmol) in tetrahydrofuran (7 ml) were reacted, giving 3-fluoro-4-[7-methoxy-3-methyl-2-oxo-8-(thiazol-5-ylmethoxy)-2,3-dihydroimidazo-[4,5-c]quinolin-1-yl]benzonitrile (15 mg, 32.5 µmol) as solid. MS: 462.0 (M+H$^+$), TLC (HPTLC): R$_f$=0.44 (ethyl acetate/ethanol 2:1, parts by volume).

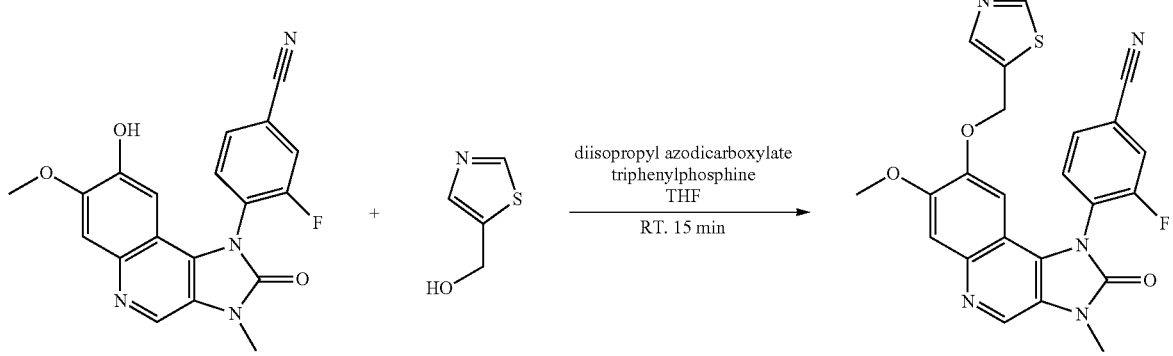

Example 3a

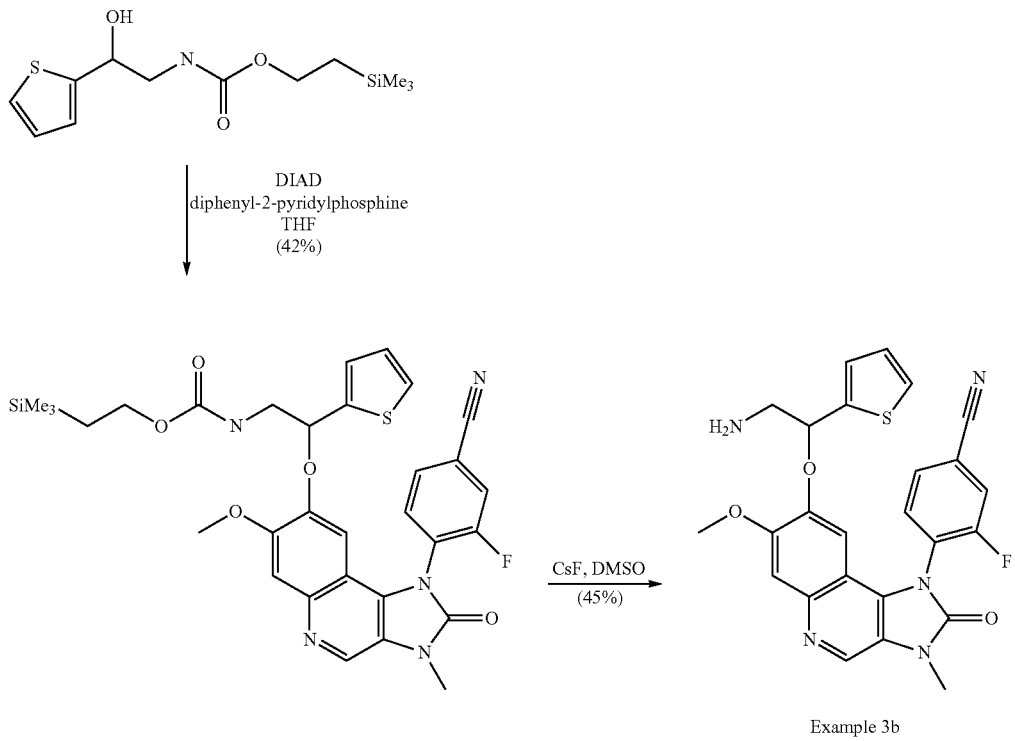

EXAMPLE 3b

Synthesis of 4-[8-(2-amino-1-thiophen-2-ylethoxy)-7-methoxy-3-methyl-2-oxo-2,3-dihydroimidazo[4,5-c]quinolin-1-yl]-3-fluorobenzonitrile 3-Fluoro-4-(8-hydroxy-7-methoxy-3-methyl-2-oxo-2,3-dihydroimidazo[4,5-c]quinolin-1-yl)-benzonitrile (350 mg, 961 µmol) and diphenyl-2-pyridylphosphine (1.46 g, 5.39 mmol) were dissolved in tetrahydrofuran (105 ml). 2-Trimethylsilanylethyl(2-hydroxy-2-thiophen-2-yl-ethyl)carbamate (787 mg, 2.74 mmol) and diisopropyl azodicarboxylate (788 µl, 4.01 mmol) were subsequently added. The reaction mixture was stirred at room temperature for 15 min. When the reaction was complete (HPLC-MS), it was added to ethyl acetate (50 ml) and saturated sodium chloride solution (50 ml) and extracted. The aqueous phase was extracted with further ethyl acetate (25 ml). The combined organic phases were washed with water (25 ml), dried over $Na_2SO_4$ and filtered. The filtrate was evaporated to dryness in vacuo, and the residue was chromatographed over flash silica gel (solvent gradient ethyl acetate/0-7% by vol. of ethanol), giving 2-trimethylsilanylethyl {2-[1-(4-cyano-2-fluorophenyl)-7-methoxy-3-methyl-2-oxo-2,3-dihydro-1H-imidazo[4,5-c]quinolin-8-yloxy]-2-thiophen-2-ylethyl}carbamate (253 mg, 399 µmol) as solid. MS: 634.2 (M+H$^+$), TLC (HPTLC): $R_f$=0.34 (ethyl acetate/ethanol 8:1, parts by volume).

2-Trimethylsilanylethyl {2-[1-(4-cyano-2-fluorophenyl)-7-methoxy-3-methyl-2-oxo-2,3-dihydro-1H-imidazo[4,5-c]quinolin-8-yloxy]-2-thiophen-2-ylethyl}carbamate (239 mg, 377 µmol) was dissolved in dimethyl sulfoxide (40 ml) under a dry nitrogen atmosphere. CsF (1.15 g, 7.60 mmol) was subsequently added, and the reaction mixture was stirred at room temperature for 18 h overnight. For work-up, the mixture was decanted off into water (300 ml), and saturated $NaHCO_3$ solution (25 ml) was added. The aqueous phase was extracted three times with ethyl acetate (100 ml each time). The combined organic phases were washed with saturated sodium chloride solution (50 ml), dried over $Na_2SO_4$ and filtered. After evaporation of the filtrate, the residue was purified by preparative HPLC (water/1-50% by vol. of acetonitrile in 15 min, flow rate 50 ml/min), giving 4-[8-(2-amino-1-thiophen-2-ylethoxy)-7-methoxy-3-methyl-2-oxo-2,3-dihydroimidazo[4,5-c]quinolin-1-yl]-3-fluorobenzonitrile (83 mg, 170 µmol) as lyophilisate after freeze-drying of the product fractions. MS: 490.1 (M+H$^+$), TLC (HPTLC): $R_f$=0.50 (methanol/iPr$_2$EtN 99:1, parts by volume).

Compounds which were prepared in accordance with the synthetic procedures from Example 3a and 3b are shown in Table 4 below.

TABLE 4

Compounds of the formulae (I) and (IA)

| No. | Structural formula | Name | Analysis | IC$_{50}$ DNA-PK [μM] |
|---|---|---|---|---|
| 30 | | 3-Fluoro-4-[7-methoxy-3-methyl-2-oxo-8-(thiazol-5-ylmethoxy)-2,3-dihydroimidazo[4,5-c]-quinolin-1-yl)benzonitrile | MS: 462.0 (M + H$^+$), TLC (HPTLC): R$_f$ = 0.44 (ethyl acetate/ethanol 2:1, parts by volume) | <0.1 |
| 31 | | 4-[8-(2-Amino-1-thiophen-2-ylethoxy)-7-methoxy-3-methyl-2-oxo-2,3-dihydroimidazo-[4,5-c]quinolin-1-yl]-3-fluorobenzonitrile | MS: 490.1 (M + H$^+$), TLC (HPTLC): R$_f$ = 50 (methanol/Hünig's base 99:1, parts by volume) | 0.1-0.5 |
| 32 | | 4-{8-[2-Amino-1-(4-fluorophenyl)ethoxy]-7-methoxy-3-methyl-2-oxo-2,3-dihydro-imidazo[4,5-c]quinolin-1-yl}-3-fluorobenzonitrile | MS: 502.1 (M + H$^+$), TLC (HPTLC): R$_f$ = 02.8 (methanol/Hünig's base 99:1, parts by volume) | 0.5-1.0 |

EXAMPLE 4a

Synthesis of 3-fluoro-4-[7-methoxy-3-methyl-2-oxo-8-(2-thiophen-3-ylethyl)-2,3-dihydroimidazo[4,5-c]quinolin-1-yl]benzonitrile 3-Fluoro-4-(8-hydroxy-7-methoxy-3-methyl-2-oxo-2,3-dihydroimidazo[4,5-c]quinolin-1-yl)-benzonitrile (162 mg, 444 μmol), N-phenyltrifluoromethanesulfonimide (317 mg, 887 μmol) and Hünig's base (300 μl, 1.76 mmol) were dissolved in N,N-dimethylformamide (15 ml). The mixture was subsequently stirred at room temperature for 30 min. For work-up, the mixture was poured into water (50 ml) and stirred for a further 30 min. The precipitate formed was then filtered off with suction and rinsed with water. The filter cake was dried at room temperature overnight in a high vacuum and chromatographed over flash silica gel (solvent gradient ethyl acetate/0-25% by vol. of ethanol), giving [1-(4-cyano-2-fluorophenyl)-7-methoxy-3-methyl-2-oxo-2,3-dihydro-1H-imidazo[4,5-c]quinolin-8-yl]trifluoromethanesulfonate (185 mg, 373 μmol) as solid. MS: 497.0 (M+H$^+$), TLC (HPTLC): R$_f$=0.49 (ethyl acetate/ethanol 2:1, parts by volume).

1-(4-Cyano-2-fluorophenyl)-7-methoxy-3-methyl-2-oxo-2,3-dihydro-1H-imidazo[4,5-c]quinolin-8-yl trifluoromethanesulfonate (119 mg, 240 μmol), 4,4,5,5-tetramethyl-2-

[(E)-2-thiophen-3-ylvinyl]-1,3,2-dioxaborolane (142 mg, 602 μmol), tripotassium phosphate (107 mg, 504 μmol) and trans-bis(tricyclohexylphosphine)palladium(II) dichloride (18 mg, 24 μmol) were dissolved in oxygen-free N,N-dimethylformamide (5 ml). The mixture was subsequently heated at 130° C. for 45 min (microwave). The reaction mixture was then filtered with suction, the filtrate was diluted with water and stirred at room temperature for 30 min. The precipitate formed was filtered off with suction and rinsed with water. The residue was chromatographed on flash silica gel (solvent gradient ethyl acetate/0-25% by vol. of ethanol), giving 3-fluoro-4-{7-methoxy-3-methyl-2-oxo-8-[(E)-2-thiophen-3-ylvinyl]-2,3-dihydroimidazo[4,5-c]quinolin-1-yl}benzonitrile (90 mg, 181 μmol) as solid. MS: 457.1 (M+H$^+$), TLC (HPTLC): R$_f$=0.47 (ethyl acetate/ethanol 2:1, parts by volume).

3-Fluoro-4-{7-methoxy-3-methyl-2-oxo-8-[(E)-2-thiophen-3-ylvinyl]-2,3-dihydroimidazo-[4,5-c]quinolin-1-yl}benzonitrile (63 mg, 138 μmol) were dissolved in ethanol (50 ml) and treated with H$_2$ on Pd/C (10%). The reaction mixture was filtered through kieselguhr with suction, rinsed, and the filtrate was evaporated to dryness. For purification, the mixture was chromatographed (preparative HPLC, solvent gradient water/1-40% by vol. of acetonitrile in 10 min, flow rate 50 ml/min), giving, after freeze-drying, 3-fluoro-4-[7-methoxy-3-methyl-2-oxo-8-(2-thiophen-3-ylethyl)-2,3-dihydroimidazo[4,5-c]quinolin-1-yl]benzonitrile (7.4 mg, 16 μmol) as lyophilisate. MS: 458.8 (M+H$^+$), TLC (HPTLC): R$_f$=0.56 (ethyl acetate/ethanol 2:1, parts by volume).

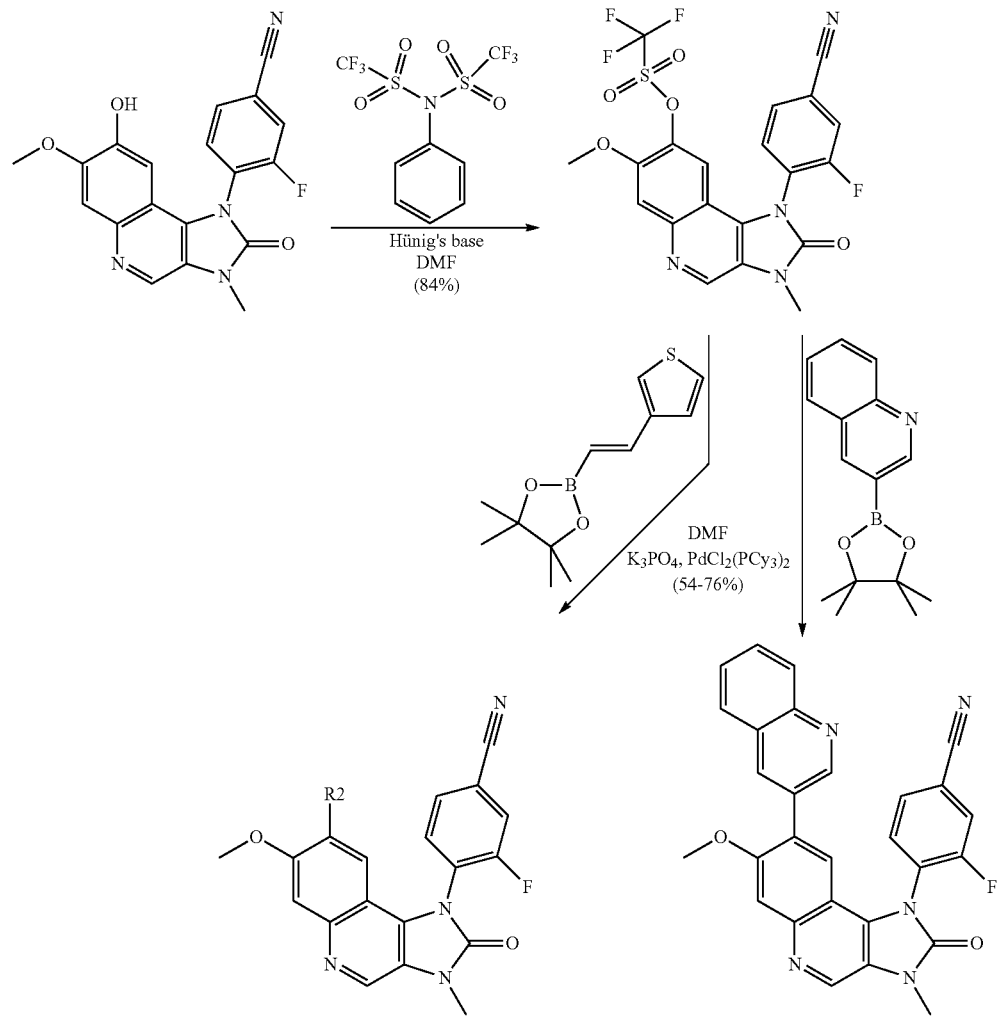

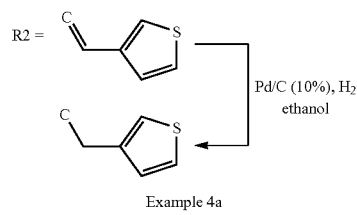

Example 4a

EXAMPLE 4b

Synthesis of 3-fluoro-4-(7-methoxy-3-methyl-2-oxo-8-quinolin-3-yl-2,3-dihydroimidazo[4,5-c]quinolin-1-yl)benzonitrile 1-(4-Cyano-2-fluorophenyl)-7-methoxy-3-methyl-2-oxo-2,3-dihydro-1H-imidazo[4,5-c]quinolin-8-yl trifluoromethanesulfonate (79 mg, 159 μmol), 3-(4,4,5,5-tetramethyl-1,3,2-dioxaborolan-2-yl)quinoline (325 mg, 1.27 mmol), tripotassium phosphate (70 mg, 319 μmol) and trans-bis(tricyclohexylphosphine)palladium(II) dichloride (35 mg, 48 μmol) were dissolved in oxygen-free N,N-dimethylformamide (4.7 ml). The reaction mixture was subsequently heated at 130° C. for 90 min (microwave). The mixture was then decanted off into water (50 ml) and stirred for a further 30 min. The precipitate formed was filtered off with suction and rinsed with water. The filter cake was subsequently suspended in a little cold dimethyl sulfoxide, filtered off and rinsed with 2-propanol, giving 3-fluoro-4-(7-methoxy-3-methyl-2-oxo-8-quinolin-3-yl-2,3-dihydroimidazo[4,5-c]quinolin-1-yl)benzonitrile (41 mg, 86 μmol) as colourless solid after drying in a high vacuum. MS: 476.1 (M+H$^+$), TLC (HPTLC): R$_f$=0.24 (ethyl acetate/ethanol 5:1, parts by volume).

$^1$H NMR (500 MHz, CDCl$_3$) δ=8.91 (d, J=2.1, 1H), 8.78 (s, 1H), 8.13 (d, J=8.4, 1H), 8.06 (d, J=1.6, 1H), 7.82 (d, J=8.1, 1H), 7.80-7.73 (m, 2H), 7.69 (t, J=8.6, 2H), 7.62 (dd, J=14.4, 6.9, 2H), 7.16 (s, 1H), 3.98 (s, 3H), 3.69 (s, 3H).

Compounds which were prepared in accordance with the synthetic procedures from Example 4a and 4b are shown in Table 5 below.

TABLE 5

Compounds of the formulae (I) and (IB)

| No. | Structural formula | Name | Analysis | IC$_{50}$ DNA-PK [μM] |
|---|---|---|---|---|
| 33 | | 3-Fluoro-4-(7-methoxy-3-methyl-2-oxo-8-pyridin-3-yl-2,3-dihydro-imidazo[4,5-c]quinolin-1-yl)-benzonitrile | MS: 426.1 (M + H$^+$), TLC (HPTLC): R$_f$ = 0.21 (ethyl acetate/ethanol 5:1, parts by volume) | <0.1 |
| 34 | | 3-Fluoro-4-[7-methoxy-8-(6-methoxypyridin-3-yl)-3-methyl-2-oxo-2,3-dihydroimidazo[4,5-c]-quinolin-1-yl)benzonitrile | MS: 456.1 (M + H$^+$), TLC (HPTLC): R$_f$ = 0.29 (ethyl acetate/ethanol 10:1, parts by volume) | <0.1 |
| 35 | | 3-Fluoro-4-(7-methoxy-3-methyl-2-oxo-8-quinolin-3-yl-2,3-dihydroimidazo[4,5-c]quinolin-1-yl)benzonitrile | MS: 476.1 (M + H$^+$), TLC (HPTLC): R$_f$ = 0.24 (ethyl acetate/ethanol 5:1, parts by volume) | <0.1 |

TABLE 5-continued

Compounds of the formulae (I) and (IB)

| No. | Structural formula | Name | Analysis | IC$_{50}$ DNA-PK [μM] |
|---|---|---|---|---|
| 36 | | 3-Fluoro-4-[7-methoxy-3-methyl-8-(1-methyl-1H-pyrazol-4-yl)-2-oxo-2,3-dihydroimidazo[4,5-c]-quinolin-1-yl]benzonitrile | MS: 429.1 (M + H$^+$), TLC (HPTLC): R$_f$ = 0.29 (ethyl acetate/ethanol 5:1, parts by volume) | <0.1 |
| 37 | | 3-Fluoro-4-[7-methoxy-3-methyl-2-oxo-8-(1H-pyrazol-4-yl)-2,3-dihydroimidazo[4,5-c]quinolin-1-yl)benzonitrile | MS: 415.1 (M + H$^+$), TLC (HPTLC): R$_f$ = 0.38 (ethyl acetate/ethanol 5:1, parts by volume) | <0.1 |
| 38 | | 3-Fluoro-4-[7-methoxy-3-methyl-8-(2-methyl-2H-pyrazol-3-yl)-2-oxo-2,3-dihydroimidazo[4,5-c]-quinolin-1-yl)benzonitrile | MS: 429.1 (M + H$^+$), TLC (HPTLC): R$_f$ = 0.22 (ethyl acetate/ethanol 5:1, parts by volume) | 0.1-0.5 |
| 39 | | 3-Fluoro-4-[7-methoxy-3-methyl-2-oxo-8-(2H-pyrazol-3-yl)-2,3-dihydroimidazo[4,5-c]quinolin-1-yl)benzonitrile | MS: 415.1 (M + H$^+$), TLC (HPTLC): R$_f$ = 0.30 (ethyl acetate/ethanol 8:1, parts by volume) | <0.1 |

TABLE 5-continued

Compounds of the formulae (I) and (IB)

| No. | Structural formula | Name | Analysis | IC$_{50}$ DNA-PK [μM] |
|---|---|---|---|---|
| 40 | | 3-Fluoro-4-[7-methoxy-3-methyl-8-(2-methyl-5-trifluoromethyl-2H-pyrazol-3-yl)-2-oxo-2,3-dihydro-imidazo[4,5-c]quinolin-1-yl]-benzonitrile | MS: 497.1 (M + H$^+$), TLC (HPTLC): R$_f$ = 0.33 (ethyl acetate/ethanol 5:1, parts by volume) | 0.1-0.5 |
| 41 | | 3-Fluoro-4-[7-methoxy-3-methyl-2-oxo-8-((E)-2-thiophen-3-yl-viniyl)-2,3-dihydroimidazo-[4,5-c]quinolin-1-yl]benzonitrile | MS: 457.1 (M + H$^+$), TLC (HPTLC): R$_f$ = 0.47 (ethyl acetate/ethanol 2:1, parts by volume) | <0.1 |
| 42 | | 3-Fluoro-4-[7-methoxy-3-methyl-2-oxo-8-(2-thiophen-3-ylethyl)-2,3-dihydroimidazo[4,5-c]-quinolin-1-yl]benzonitrile | MS: 458.8 (M + H$^+$), TLC (HPTLC): R$_f$ = 0.56 (ethyl acetate/ethanol 2:1, parts by volume) | 0.1-0.5 |

TABLE 5-continued

Compounds of the formulae (I) and (IB)

| No. | Structural formula | Name | Analysis | IC$_{50}$ DNA-PK [µM] |
|---|---|---|---|---|
| 43 | | 3-Fluoro-4-[7-methoxy-3-methyl-2-oxo-8-((E)-styryl)-2,3-dihydroimidazo[4,5-c]quinolin-1-yl]benzonitrile | MS: 451.1 (M + H$^+$), TLC (HPTLC): R$_f$ = 0.46 (ethyl acetate/ethanol 2:1, parts by volume) | 0.1-0.5 |

EXAMPLE 5

DNA-PK/Biochemical Assay

The kinase assay was carried out in streptavidin-coated 348-well microtitre FlashPlates®. To this end, 1.5 µg of the DNA-PK/protein complex and 100 ng of biotinylated substrate, such as, for example, PESQEAFADLWKK biotin-NH2 ("biotin-DNA-PK peptide"), in a total volume of 36.5 µl (34.25 mM HEPES/KOH, 7.85 mM Tris-HCl, 68.5 mM KCl, 5 µM ATP, 6.85 mM MgCl$_2$, 0.5 mM EDTA, 0.14 mM EGTA, 0.69 mM DTT, pH 7.4), were incubated at room temperature for 90 min with 500 ng of DNA from calf thymus, 0.1 µCi of 33P-ATP and 1.8% of DMSO per well with or without the test compound. The reaction was stopped using 50 µl/well of 200 mM EDTA. After incubation for a further 30 min at room temperature, the liquid was removed. Each well was washed three times with 100 µl of 0.9% sodium chloride solution. A non-specific reaction (blank value) was determined using 10 µM of a proprietary kinase inhibitor. The radioactivity measurement was carried out by means of a TopCount. IC$_{50}$ values were calculated in RS1 (Kashishian et al. (2003) Molecular Cancer Therapeutics 1257).

EXAMPLE 6

Cellular DNA-PK phosphorylation at serine 2056

HCT116 cells were cultivated in MEM alpha medium with 10% of foetal calf serum, 1 mM sodium pyruvate and 2 mM glutamine at 37° C. and 10% CO$_2$. The cells were detached from the base of the culture vessels with the aid of trypsine/EDTA, centrifuged off in centrifuge tubes and taken up in fresh medium. The cell density was subsequently determined. 200,000 cells were sown per cavity of a 12-well cell culture plate in 1 ml of culture medium and cultivated overnight. Next day, 10 µM bleomycin and test substances in fresh culture medium was added to the cells and these were cultivated for a further six hours. Cell lysis was subsequently carried out. The cell lysates were investigated by SDS polyacrylamide gel electrophoresis by means of DNA-PK-specific antibodies (Abcam ab13852: total DNA-PK; ab18192: phosphoserine 2056 DNA-PK) and Western Blotting. The enzymatic reaction was developed with the aid of a chemiluminescence reagent. The chemiluminescence was recorded with the aid of a documentation system (VersaDoc™, Bio-Rad, USA) and evaluated densitometrically with the aid of instrument-specific software (Quantity One). The signals with phospho-DNA-PK-specific antibodies were standardised to the signal with the antibody against the total protein DNA-PK. IC$_{50}$ values and percentage inhibition data were determined by referencing to the signal level of the bleomycin-treated vehicle control group.

EXAMPLE 7

Cellular Colony Growth Test

The colorectal carcinoma cell line HCT116 was cultivated in MEM alpha medium with 10% of foetal calf serum, 1 mM sodium pyruvate and 2 mM glutamine at 37° C. and 10% CO$_2$. The cells were detached from the base of the culture vessels with the aid of trypsine/EDTA, centrifuged off in centrifuge tubes and taken up in fresh medium. The cell density was subsequently determined. 300 cells were sown out in 6-well cell culture plates in 2 ml of culture medium and cultivated overnight. Next day, the cells were treated with test substances for one hour before the cell culture plates were treated with defined doses of X-rays (in general 0, 2.4, 4.8, 12 Gray; irradiation instrument: Faxitron RX-650; Faxitron X-Ray LLC, USA). In order to determine the dose/effect relationships, the cells were treated with various concentrations of a test substance. After irradiation, the cells are cultivated for a further 24 hours in the presence of the test substance, the culture medium was then replaced with culture medium without test substance, and the cells were cultivated for a further 6-8 days. The cell colonies formed were subsequently stained with the aid of Crystal Violet and counted in a colony counter (Gelcount, Oxford Optronics, UK). Dose/effect curves, in particular IC$_{50}$ values, were determined using a curve adaptation function for nonlinear dose/effect relationships.

EXAMPLE 8

Cellular CHK2 phosphorylation at threonine 68

HCT116 cells were cultivated in MEM alpha medium with 10% of foetal calf serum, 1 mM sodium pyruvate and 2 mM glutamine at 37° C. and 10% CO2. The cells were detached from the base of the culture vessels with the aid of trypsine/EDTA, centrifuged off in centrifuge tubes and taken up in fresh medium. The cell density was subsequently determined. 50,000 cells were sown per cavity of a 96-well cell culture plate in 0.1 ml of culture medium and cultivated overnight. Next day, 10 µM bleomycin and test substances in fresh culture medium were added to the cells and these were cultivated for a further six hours. After lysis of the cells, phospho-threonine 68 of the CHK2 kinase was detected in the lysates with the aid of a phospho-CHK2 (Thr68)-specific ELISA detection system (Catalogue No. 7037, Cell Signaling Technologies, USA). The ELISA colour reaction was measured spectrophotometrically at 450 nm. The extinction of the unstimulated controls (vehicle control without bleomycin) was subtracted from the extinction values of the treatment groups. The controls which were treated with bleomycin were set equal to 100% and all other extinction values were set in relation thereto. $IC_{50}$ values were determined with the aid of the GraphPad Prism statistics program (GraphPad Software, USA) or Assay Explorer (Symyx Technologies Inc., USA).

EXAMPLE 9

Pharmaceutical Compositions

Example A

Injection Vials

A solution of 100 g of active compound according to the invention and 5 g of disodium hydrogenphosphate in 3 l of bidistilled water was adjusted to pH 6.8 using 2 N hydrochloric acid, sterile-filtered, transferred into injection vials, lyophilised under sterile conditions and sealed under sterile conditions. Each injection vial contained 5 mg of active compound according to the invention.

Example B

Suppositories

A mixture of 20 g of active compound according to the invention with 100 g of soya lecithin and 1400 g of cocoa butter was melted, poured into moulds and allowed to cool. Each suppository contained 20 mg of active compound according to the invention.

Example C

Solution

A solution was prepared from 1 g of active compound according to the invention, 9.38 g of $NaH_2PO_4*2\ H_2O$, 28.48 g of $Na_2HPO_4*12\ H_2O$ and 0.1 g of benzalkonium chloride in 940 ml of bidistilled water. The pH was adjusted to 6.8, and the solution was made up to 1 l and sterilised by irradiation. This solution could be used in the form of eye drops.

Example D

Ointment 500 mg of active compound according to the invention were mixed with 99.5 g of Vaseline under aseptic conditions.

Example E

Tablets

A mixture of 1 kg of active compound according to the invention, 4 kg of lactose, 1.2 kg of potato starch, 0.2 kg of talc and 0.1 kg of magnesium stearate was pressed in a conventional manner to give tablets in such a way that each tablet contained 10 mg of active compound according to the invention.

Example F

Dragees

Tablets were pressed analogously to Example E and then coated in a conventional manner with a coating of sucrose, potato starch, talc, tragacanth and dye.

Example G

Capsules 2 kg of active compound according to the invention were introduced into hard gelatine capsules in a conventional manner in such a way that each capsule contained 20 mg of active compound according to the invention.

Example H

Ampoules

A solution of 1 kg of active compound according to the invention in 60 l of bidistilled water was sterile-filtered, transferred into ampoules, lyophilised under sterile conditions and sealed under sterile conditions. Each ampoule contained 10 mg of active compound according to the invention.

Example I

Inhalation Spray 14 g of active compound according to the invention were dissolved in 10 l of isotonic NaCl solution, and the solution was transferred into standard commercial spray vessels with pump mechanism. The solution could be sprayed into mouth or nose. One spray shot (approx. 0.1 ml) corresponded to a dose of approx. 0.14 mg.

The invention claimed is:
1. A compound of formula (II)

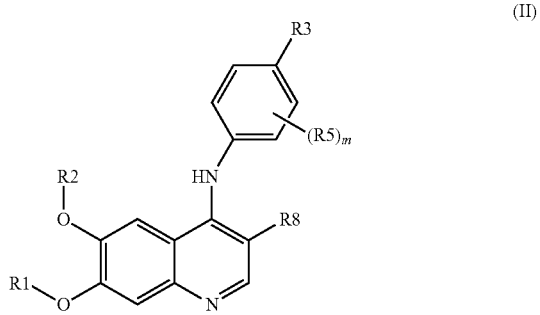

(II)

in which
R1 denotes Y or —$(CY_2)_n$—Ar,
R2 denotes Y, —$(CY_2)_p$—(C[YR6])$_s$—R7 or -alk-R7, R3 denotes Y or CN, R5 denotes A, Hal, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY, R6 denotes Y, Hal, —(CY$_2$)$_n$—NYY, —(CY$_2$)$_n$—NY—COO —(CY$_2$)$_n$—SiA$_3$—(CY$_2$)$_n$—COOY, —CO—NYY, —CO—NY—(CY$_2$)$_n$—OY, —CO—NY—(CY$_2$)$_n$—NYY or SO$_2$A, R7 denotes —(CY$_2$)$_p$—Ar or —(CY$_2$)$_p$-Het$^1$, Y denotes H or A, A denotes unbranched or branched alkyl having 1, 2, 3, 4, 5, 6, 7, 8, 9 or 10 C atoms, where 1, 2, 3, 4, 5, 6 or 7 H atoms may be replaced, independently of one another, by Hal, Alk denotes alkenyl having 2, 3, 4, 5 or 6 C atoms, where 1, 2, 3 or 4 H atoms may be replaced, independently of one another, by Hal and/or OY, Ar denotes phenyl which is unsubstituted or mono-, di- or trisubstituted by Hal, A, CN, —(CY$_2$)$_p$—OY, —(CY$_2$)$_p$—NYY, —(CY$_2$)$_p$—COOY, —(CY$_2$)$_p$—CO—NYY or —(CY$_2$)$_p$—NY—COY, Het$^1$ denotes mono- or bicyclic heteroaryl having 2, 3, 4, 5, 6, 7, 8 or 9 C atoms and 1, 2, 3 or 4 N, O and/or S atoms, which may be unsubstituted or mono-, di- or trisubstituted by Hal, A, CN, —(CY$_2$)$_p$—OY, —(CY$_2$)$_p$—NYY, —(CY$_2$)$_p$—COOY, —(CY$_2$)$_p$—CO—NYY, —(CY$_2$)$_p$—NY—COY or —SO$_2$-Het$^2$, Het$^2$ denotes a monocyclic saturated heterocycle having 2, 3, 4, 5, 6 or 7 C atoms and 1, 2, 3 or 4 N, O and/or S atoms, which may be unsubstituted or monosubstituted by A, Hal denotes F, Cl, Br or I, m denotes 0, 1, 2, 3 or 4, and n, p, s, independently of one another, denote 0, 1, 2, 3, 4, 5 or 6, and R8 denotes NYY, and/or salts, tautomers and/or stereoisomers thereof, including mixtures thereof in all ratios.

2. A compound according to claim 1 in which

R1 denotes A,

R2 denotes A or —(CH$_2$)$_p$—(CH$_2$)$_s$—Ar,

R3 denotes CN,

R5 denotes Hal,

R8 denotes NH$_2$,

A denotes unbranched or branched alkyl having 1, 2, 3 or 4 C atoms, where 1, 2 or 3 H atoms may be replaced, independently of one another, by Hal, Ar denotes phenyl which is unsubstituted or mono- or disubstituted by Hal, Hal denotes F, Cl, Br or I, and m, p, s, independently of one another, denote 0, 1 or 2, and/or salts, tautomers and/or stereoisomers thereof, including mixtures thereof in all ratios.

3. A process for the preparation of a compound of the formula (II) according to claim 1 and/or salts, tautomers and/or stereoisomers thereof, including mixtures thereof in all ratios, comprising:

(a) reacting a compound of formula (III)

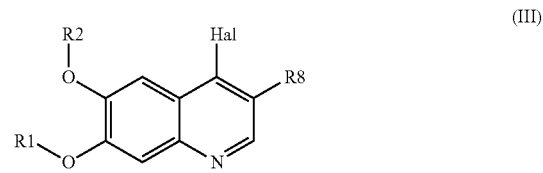

in which

Hal denotes F, Cl, Br or I, and

R1, R2 and R8 have the meaning indicated in claim 1, with a compound of formula (IV)

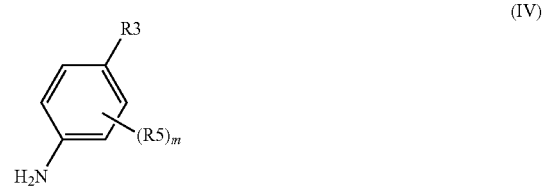

in which R3, R5 and m have the meaning indicated in claim 1, to give a compound of formula (II)

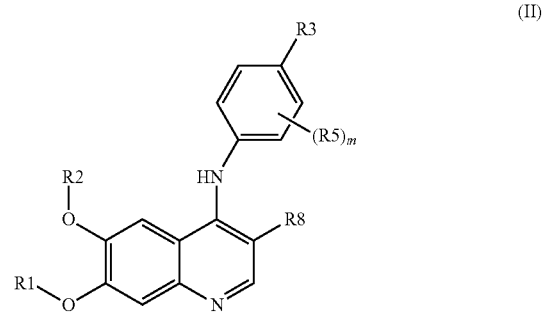

in which R1, R2, R3, R5, R8 and m have the meaning indicated in claim 1, and optionally (b) converting a base or acid of a compound of formula (II) into one of its salts.

* * * * *